US011191777B2

(12) United States Patent
Hedrick et al.

(10) Patent No.: US 11,191,777 B2
(45) Date of Patent: Dec. 7, 2021

(54) ANTIMICROBIAL GUANIDINIUM MACROMOLECULES WITH BACTERIA TARGETING MOIETIES

(71) Applicants: International Business Machines Corporation, Armonk, NY (US); Agency for Science, Technology and Research, Singapore (SG)

(72) Inventors: James L. Hedrick, Pleasanton, CA (US); Yi Yan Yang, Singapore (SG); Nathaniel H. Park, San Jose, CA (US); Victoria A. Piunova, Los Gatos, CA (US); Zhi Xiang Voo, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 218 days.

(21) Appl. No.: 16/013,499

(22) Filed: Jun. 20, 2018

(65) Prior Publication Data

US 2019/0388460 A1 Dec. 26, 2019

(51) Int. Cl.
*A61K 31/765* (2006.01)
*A61K 31/155* (2006.01)
*C08K 5/31* (2006.01)
*C08L 69/00* (2006.01)

(52) U.S. Cl.
CPC .......... *A61K 31/765* (2013.01); *A61K 31/155* (2013.01); *C08K 5/31* (2013.01); *C08L 69/00* (2013.01)

(58) Field of Classification Search
None
See application file for complete search history.

(56) References Cited

U.S. PATENT DOCUMENTS

| 9,854,806 | B2 * | 1/2018 | Chin | A61P 31/00 |
| 2007/0048345 | A1 | 3/2007 | Huang et al. | |
| 2012/0301528 | A1 | 11/2012 | Uhlmann et al. | |
| 2014/0301967 | A1 | 10/2014 | Chin et al. | |
| 2015/0264932 | A1 | 9/2015 | Coady et al. | |
| 2016/0338356 | A1 * | 11/2016 | Chin | C08G 18/73 |
| 2017/0073471 | A1 | 3/2017 | Breyta et al. | |
| 2017/0150714 | A1 | 6/2017 | Schwarz | |
| 2017/0303541 | A1 | 10/2017 | Chin et al. | |
| 2019/0390005 | A1 * | 12/2019 | Hedrick | A61P 31/04 |

OTHER PUBLICATIONS

Pranantyo et. al, "Increasing bacterial affinity and cytocompatibility with four-arm star glycopolymers and antimicrobial α-polylysine", Polymer Chemistry, 8, pp. 3364-3373, 2017 (Year: 2017).*

List of IBM Patents or Applications Treated as Related.
Chin, et al., "A macromolecular approach to eradicate multidrug resistant bacterial infections while mitigating drug resistance onset," Nature Communications | (2018) 9:917, DOI: 10.1038/s41467-018-03325-6, 14 pages.
Cho, et al., "Molecular Weight and Charge Density Effects of Guanidinylated Biodegradable Polycarbonates on Antimicrobial Activity and Selectivity," DOI: 10.1021/acs.biomac.7b01245, 13 pages.
Engler, et al., "Antimicrobial Polycarbonates: Investigating the Impact of Balancing Charge and Hydrophobicity Using a Same-Centered Polymer Approach," Biomacromolecules, 2013, 14 (12), 2 pages.
Nimmagadda, et al., "Polycarbonates with Potent and Selective Antimicrobial Activity toward Gram-Positive Bacteria," Biomacromolecules, Jan. 9, 2017; 18(1): 87-95. doi:10.1021/acs.biomac.6b01385, 24 pages.
Tejero, et al., "Tailoring Macromolecular Structure of Cationic Polymers towards Efficient Contact Active Antimicrobial Surfaces," Polymers 2018, 10, 241; doi:10.3390/polym10030241, 11 pages.
Liu, et al., "Highly potent antimicrobial polyionenes with rapid killing kinetics, skin biocompatibility and in vivo bactericidal activity," Biomaterials 127 (2017) pp. 36-48.
Pratt, et al., "Exploration, Optimization, and Application of Supramolecular Thiourea-Amine Catalysts for the Synthesis of Lactide (Co)polymers," Macromolecules 2006, 39, pp. 7863-7871.
Cooley, et al., "Oligocarbonate Molecular Transporters: Oligomerization-Based Syntheses and Cell-Penetrating Studies," J. Am. Chem. Soc. 2009, 131, pp. 16401-16403.
Pratt, et al., "Tagging alcohols with cyclic carbonate: a versatile equivalent of (meth)acrylate for ring-opening polymerization," The Royal Society of Chemistry 2007, 5 pages.
Xue, et al., "Antimicrobial Polymeric Materials with Quaternary Ammonium and Phosphonium Salts," Int. J. Mol. Sci. 2015, 16, pp. 3626-3655; doi:10.3390/ijms16023626.
Yang, et al., "Broad-Spectrum Antimicrobial Star Polycarbonates Functionalized with Mannose for Targeting Bacteria Residing inside Immune Cells," Advanced Healthcare Materials, vol. 5, Issue 11 Jun. 8, 2016, 2 pages, https://onlinelibrary.wiley.com/doi/abs/10.1002/adhm.201600070.
Non-Final Office Action received for U.S. Appl. No. 16/013,474 dated Jun. 8, 2020, 45 pages.
Final Office Action received for U.S. Appl. No. 16/013,474 dated Oct. 22, 2020, 26 pages.

* cited by examiner

*Primary Examiner* — Robert T. Crow
*Assistant Examiner* — John P Nguyen
(74) *Attorney, Agent, or Firm* — Amin, Turocy & Watson, LLP

(57) ABSTRACT

Compositions and methods regarding antimicrobial guanidinium macromolecules with one or more targeting moieties for selectively targeting bacteria are provided. According to an embodiment, an antimicrobial macromolecule is provided that comprises a polymer backbone and one or more guanidinium moieties that extend from the polymer backbone. The antimicrobial macromolecule further comprises a targeting moiety that extends from the polymer backbone. The targeting moiety can comprise a substance favored for consumption by bacteria, such as a monosaccharide.

8 Claims, 15 Drawing Sheets

Example Protected Monosaccharides

202 → 1,2:3,4-Di-O-isopropylidene-alpha-D-galactopyranose

204 → 1,2:5,6-Di-O-isopropylidene-alpha-D-glucofuranose

201 → 2,3:5,6-Di-O-isopropylidene-a-D-mannofuranose

203 → 2,3:4,5-Di-O-isopropylidene-beta-D-fructopyranose

Cumulative Distribution of MIC Values Against Clinically Isolated MDR A. baumannii (n=10)

| Agent | MIC Values (μg/mL) | | | | | | | | | | |
|---|---|---|---|---|---|---|---|---|---|---|---|
| | 1 | 2 | 4 | 8 | 16 | 32 | 64 | 128 | 256 | ≥512 |
| Dp20 | | | 40 | 20 | 60 | 90 | 100 | | | |
| Mannose_16 | | | | 80 | 100 | | | | | |
| Glucose_17 | | | 20 | 50 | 90 | 100 | | | | |
| Ceftriaxone | | | | | | 10 | 20 | 60 | 80 | 100 |
| Gentamicin | | | | | | | 30 | 60 | 100 | |
| Imipenem | | | | | | 40 | 50 | 100 | | |

FIG. 5

MICs Against Clinically Isolated MDR Bacteria Strains, Including: K. pneumoniae (KP), E. coli (EC), A. baumannii (AB), and methicillin-resistant S. aureus (MRSA)

| Agent | KP 7958 | KP 9170 | EC 56809 | EC 58628 | AB 4123 | AB 10361 | MRSA 25312 | MRSA 25332 | MRSA 25343 |
|---|---|---|---|---|---|---|---|---|---|
| DP20 | 64 | 64 | 16 | 32 | 16 | 16 | 8 | 16 | 16 |
| Mannose_16 | 32 | 32 | 16 | 16 | 4 | 8 | 4 | 8 | 8 |
| Glucose_17 | 32 | 32 | 16 | 32 | 8 | 8 | 4 | 4 | 8 |
| Imipenem | 64 | 64 | 0.25 | 0.25 | 32 | 32 | -- | -- | -- |
| Vancomycin | -- | -- | -- | -- | -- | -- | 2 | 2 | 2 |

FIG. 6

$ED_{50}$ (effective dose that cures 50% infected mice) and $ED_{95}$ (effective dose that cures 95% infected mice) of mannose_16, glucose_17, Dp20 and the imipenem control

| Agent | $ED_{50}$ (mg/kg) | 95% Confidence Index | $ED_{95}$ (mg/kg) |
|---|---|---|---|
| Imipenem | 8.11 | 5.74-11.6 | 23.0 |
| DP20 | 8.39 | 3.62-9.08 | 21.5 |
| Mannose_16 | 5.56 | 3.25-8.19 | 20.5 |
| Glucose_17 | 6.62 | 4.20-9.33 | 19.5 | ations. Its sole purpose is to
ANTIMICROBIAL GUANIDINIUM MACROMOLECULES WITH BACTERIA TARGETING MOIETIES

TECHNICAL FIELD

The subject disclosure relates to antimicrobial macromolecules and more particularly to one more guanidinium macromolecules with one or more targeting moieties for selectively targeting bacteria.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding antimicrobial guanidinium macromolecules with one or more targeting moieties for selectively targeting bacteria are described.

According to an embodiment, an antimicrobial macromolecule is provided. The antimicrobial macromolecule can comprise a polymer backbone, one or more guanidinium moieties that extend from the polymer backbone, and a targeting moiety that extends from the polymer backbone. The targeting moiety can comprise a substance favored for consumption by bacteria, such as a monosaccharide. For example, in one or more implementations, the targeting moiety is selected from a group consisting of mannose and glucose. In some implementations, the polymer backbone of the antimicrobial macromolecule comprises polycarbonate. In other implementations, the polymer backbone can be selected from a group consisting of polylysine, polyionene, and polyethylene imine.

The subject antimicrobial macromolecule is highly effective at killing Gram-negative bacteria and Gram-positive bacteria. For example, in various example implementations, the antimicrobial macromolecule is effective at killing multidrug resistant (MDR) bacteria selected from a group consisting of: *Acinetobacter baumannii, Klebsiella pneumonia, Escherichia coli, Staphylococcus aureus*, methicillin-resistant *Staphylococcus aureus*, and *Pseudomonas aeruginosa*. The antimicrobial macromolecule further exhibits low toxicity in mammalian cells demonstrated by a red blood cell viability level greater than 95% at an effective dose. Moreover, the antimicrobial macromolecule is attributed to less than a 1% development of bacterial antimicrobial agent resistance at an effective dose over at least 20 passages.

In another embodiment a method is provided. The method can comprise dissolving a monosaccharide with a guanidinium functionalized monomer in a solvent, and polymerizing the guanidinium functionalized monomer to form a polymer, wherein the polymer comprises a plurality of covalently bonded units of the guanidinium functionalized monomer and a least two peripheral ends, wherein at least one unit of the monosaccharide is covalently bound to at least one of the peripheral ends. In one or more implementations, the monosaccharide comprises a protected monosaccharide and wherein the guanidinium functionalized monomer comprises cyclic carbonate with a protected guanidinium moiety bound to the cyclic carbonate via a spacer group. In accordance with these implementations, the polymerizing comprises an organocatalyzed ring opening polymerization of the cyclic carbonate using the protected monosaccharide as an initiator. The method can further comprise removing protection groups from the protected monosaccharide and the protected guanidinium moiety, thereby forming a deprotected polymer, wherein the deprotected polymer is effective at killing Gram-negative bacteria and Gram-positive bacteria.

BRIEF DESCRIPTION OF THE DRAWINGS

FIG. 5 presents an example, non-limiting table providing the cumulative distribution of minimum inhibitory concentration (MIC) values of various antimicrobials, including the subject antimicrobial guanidinium macromolecules, against clinically isolated. MDR (MDR) *Acinetobacter baumannii* (*A. baumannii*) in accordance with one or more embodiments described herein.

FIG. 6 presents an example, non-limiting table comparing the MIC values of various antimicrobials, including the subject antimicrobial guanidinium macromolecules, against different strains of clinically isolated bacterial in accordance with one or more embodiments described herein.

DETAILED DESCRIPTION

Figure 1:
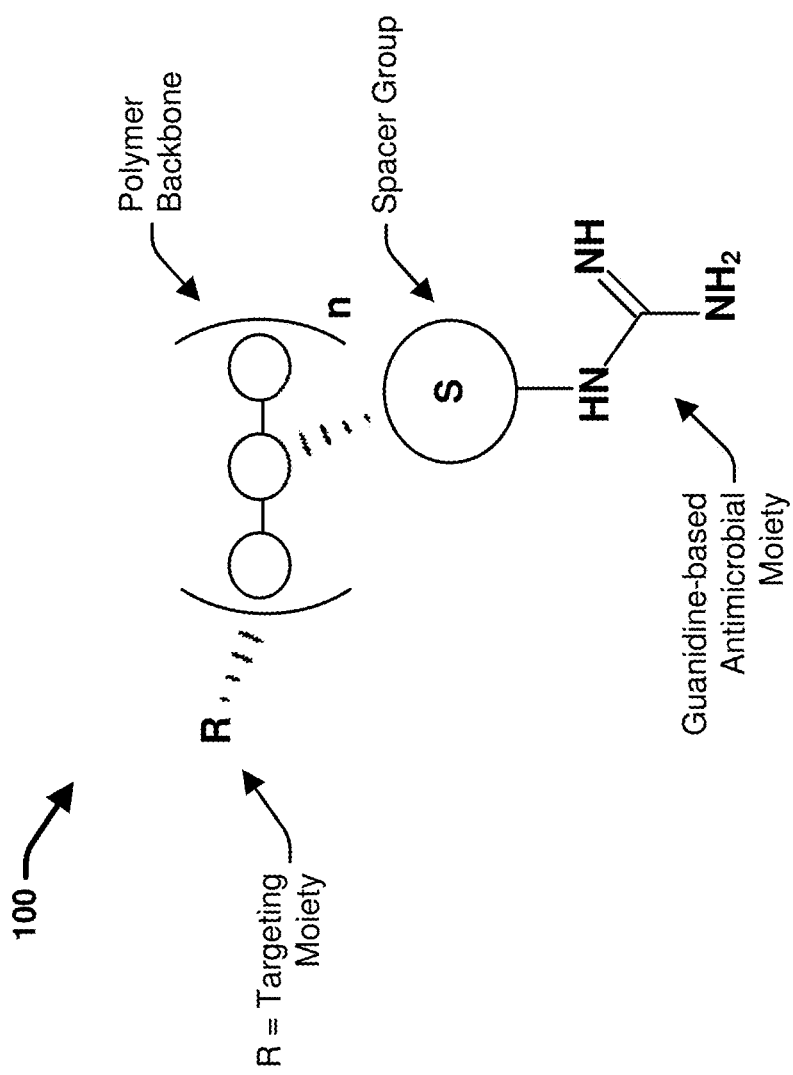
FIG. 1 illustrates a diagram of an example, non-limiting chemical structure that can characterize one or more antimicrobial guanidinium macromolecules in accordance with one or more embodiments described herein.

The following detailed description is merely illustrative and is not intended to limit embodiments and/or application or uses of embodiments. Furthermore, there is no intention to be bound by any expressed or implied information presented in the preceding Summary and Brief Description of the Drawings sections, or in the Detailed Description section.

Over the last few decades, the emergence of antibiotic/pharmaceutical-resistance amongst pathogens such as *Acinetobacter baumannii* (*A. baumannii*) and *Klebsiella pneumonia* (*K. pneumonia*) has become increasingly prevalent. Despite best efforts, the panacea for these recalcitrant infections has not been found. With no effective and safe treatments available, MDR infections are fast morphing into a global healthcare threat. Polymixins remain the last line treatment for these MDR infections although they are associated with significant adverse effects (nephrotoxicity and neurotoxicity) and are ineffective against Gram-positive bacteria. There is thus a dire need to develop novel antimicrobial compounds that have both potent and a broad spectrum of activity (against Gram-positive and Gram-negative bacteria), yet at the same time, well-tolerated with low propensity for resistance development.

The disclosed subject matter is directed the development and application of one or more novel guanidinium based antimicrobial macromolecules capable of selectively targeting and eradicating MDR bacteria, in vitro and in vivo, while minimizing toxicity and resistance onset. In some implementations, the disclosed guanidinium macromolecules can also be effective at killing fungi, yeast, and other pathogens. In one or more embodiments, the subject antimicrobial guanidinium-based macromolecules can comprise one or more targeting moieties attached to a guanidinium functionalized polymer. The guanidinium functionalized polymer can comprise a polymer backbone with one or more antimicrobial guanidinium moieties that extend therefrom. In some implementations, the polymer backbone can comprise a polycarbonate. However, other suitable polymers can be employed for the polymer backbone, such as but not limited to, polylysine, polyionene, polyethylene imine and the like. In various embodiments, the guanidinium functionalized polymer can facilitate killing bacterial cells via an electrostatic interaction mechanism. In this regard, the guanidinium moieties can be cationic (positively charged) in nature and configured to bind with and neutralize the anionic (negatively charged) bacterial surface, resulting in a charge neutralization that allows the macromolecule to translocate through the bacterial membrane (e.g., as a non-polar species). The macromolecule is then released through the membrane leading to cytosol precipitation and subsequent bacterial cell apoptosis.

The one or more targeting moieties of the subject guanidinium functionalized polymers can comprise a substance that is favored for consumption by Gram-negative and Gram-positive bacteria. In this regard, the targeting moiety can selectively attract bacterial cells and facilitate increasing the efficiency of the attachment of the macromolecule to the bacterial surface and subsequent translocation of the guanidinium functionalized polymer through the bacterial cell membrane. For example, in various embodiments, the one or more targeting moieties can comprise carbohydrate moieties (e.g., sugars). The sugar targeting moiety has been shown to enhance bacterial targeting and antimicrobial activity of the entire macromolecule, increase solubility of the macromolecule, and further mitigate toxicity. Moreover, targeting moieties that comprise sugars have been shown to target the bacteria cell wall/membrane in such a way that the sugar gets taken up and chemically incorporated into the bacterial cell wall/membrane. Accordingly, in addition to facilitating targeting selectivity and antimicrobial efficiency of the guanidinium based macromolecule, the sugar moiety can further contribute to local disorder and stress within the lipid bilayer of the bacterial cell, leading to the membrane damage and thus a higher rate of cell lysis/apoptosis. This approach may also be used to engineer the wall/membrane for smart and targeted therapies or diagnostics.

Some example compounds comprising a polycarbonate polymer backbone functionalized with guanidinium moieties and further comprising a single unit of glucose or mannose as the targeting moiety were tested in vitro and in vivo (in a blood infection animal model) with substantially greater success over traditional antibiotics. Relative to leading antibiotics including ceftriaxone, gentamicin, imipenem, and levofloxacin, the example compounds exhibited higher efficacy at killing both Gram-negative and Gram-positive MDR bacteria at substantially lower minimum inhibitory concentration (MIC) values and lower effective doses. The example compounds also exhibited extremely low toxicity against red blood cells with red blood cell (RBC) hemolysis viability levels at or near 100%, even at concentrations up to 1000 parts per million (ppm). In addition, unlike the commercial antibiotics, the example compounds failed to engender antimicrobial resistance over many passages. The sample compounds also demonstrated increased efficacy, reduced effective dose amounts, reduced toxicity and strong immunity to development of antimicrobial resistance relative to guanidinium functionalized polymers without the disclosed targeting moieties and associated chemical structure.

Additionally, the subject guanidinium-based macromolecules can be biocompatible, biodegradable, non-hemolytic, and non-cytotoxic at concentrations above the MIC. The subject guanidinium-based macromolecules are therefore attractive for a wide range of consumer products, such as for example, antibiotic pharmaceuticals, cosmetics, skin lotions, and the like. The term biodegradable is defined by the American Society for Testing and Materials (ASTM) as degradation caused by biological activity, especially by enzymatic action, leading to a significant change in the chemical structure of the material. For purposes herein, the subject guanidinium-based macromolecules having (and variations thereof) can be characterized as biodegradable because they have been shown to undergo at least 60% biodegradation within 180 days, in accordance with ASTM D6400. The subject guanidinium-based macromolecules can also be characterized as enzymatically biodegradable because they have been shown to be degraded (e.g., depolymerized) by a reaction catalyzed by an enzyme. A biocompatible material is defined herein as a material capable of performing with an appropriate hos response in a specific application.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a diagram of an example, non-limiting chemical Structure 100 that can characterize one or more antimicrobial guanidinium macromolecules in accordance with one or more embodiments described herein. Structure 100 comprises a polymer backbone with a targeting moiety "R" extending therefrom. In this regard, the targeting moiety R can be covalently bonded to one or more atoms of the polymer backbone. In the embodiment shown, the polymer backbone can comprise one or more polymer units (represented by the series of connected circles within parenthesis) respectively including a guanidine-based functional group extending therefrom and covalently bonded to one or more atoms of the polymer unit. In this regard, the polymer backbone can comprise one or more repeat monomer units that are respectively functionalized with a guanidine-based antimicrobial moiety. These monomers are referred to herein as guanidinium functionalized monomers. The guanidinium functional group comprises a guanidine-based antimicrobial moiety that can be connected to the polymer backbone via at least one spacer group "S." The number "n" of repeating and connected/bonded guanidinium functionalized monomer units that form the polymer backbone can vary. For example, in some implementations, the number n of repeating monomer units can be one or more and one thousand or less. However, in one or more exemplary embodiments, the number n of repeating monomer units is between 5 and 40 units. In another embodiment, the number n of repeating monomer units is between 10 and 30 units. Still in yet another embodiment, the number n of repeating units is between 15 and 25 units, with an optimal number of units being 20 units.

In the embodiment shown, each monomer unit of the polymer backbone includes at least one guanidinium functional group that consists of the guanidine-based antimicrobial moiety connected to thereto via the spacer group S. However, in some implementations, one or more of the monomer units can include no guanidinium functional groups and/or one or more of the monomer units can include two or more guanidinium based functional groups. In this regard, no restriction is placed on the polymer skeletal structure of the skeletal backbone. Exemplary non-limiting polymer skeletal structures can include linear polymers, branched polymers, star polymers, mykto-arm star polymers, latter polymers, cyclic polymers, and graft polymers. The forgoing polymer types can comprise a homopolymer, a random copolymer, or a block copolymer chain. In various exemplary embodiments, the antimicrobial guanidinium based macromolecule is a linear polymer comprising a plurality of covalently bonded guanidinium functionalized monomer units. Herein, a linear polymer has one branch having two peripheral ends (i.e., dangling ends, as the two ends of a segment of a rope). At least one of the peripheral ends can comprise a targeting moiety R covalently bonded thereto. The one branch can comprise one or more polymer chain segments covalently linked together at respective polymer chain ends by way of any suitable linking group, which can include a single bond. Each polymer chain segment of a linear polymer can comprise a homopolymer, random copolymer, or block copolymer chain comprising one or more repeat units. At least one of the polymer chain segments comprises one or more repeat units of the guanidinium functionalized monomer.

The targeting moiety R, the polymer backbone, the spacer group S and the chemical structure of the guanidine-based antimicrobial moiety can vary. In various embodiments, the targeting moiety R can include a substance that is favored for consumption by bacteria. In this regard, the targeting moiety R can selectively attract bacteria to facilitate the consumption and translocation of the subject guanidinium-based macromolecules into the bacterial cytosol and/or integration of the targeting moiety R into the bacterial cell wall/membrane. In one or more embodiments, the targeting moiety R can comprise one or more carbohydrates (also referred to as saccharides). For example, in some implementations, the targeting moiety R can comprise one or more sugars, including monosaccharides and disaccharides. Some suitable sugars for the targeting moiety R can include but are not limited to, fructose, galactose, glucose, and/or mannose. In some implementations, the targeting moiety R can be a single unit of sugar. As exemplified infra, some example guanidinium-based macromolecules having Structure 100 and employing only a single unit of sugar for the targeting moiety R have demonstrated substantially higher antimicrobial efficacy relative to guanidinium functionalized polymers without a targeting moiety R, as well leading antibiotics including ceftriaxone, gentamicin, and imipenem. In other implementations, the targeting moiety R can include plurality of sugar units.

In some embodiments, the targeting moiety R can comprise or be initiated from a protected monosaccharide. Protected monosaccharides include sugars in which at least one hydroxyl group is protected by some form of modification. With these embodiments, usage of a protected sugar as the targeting moiety R (or to initialize the targeting moiety R) can minimize the synthesis complexity of the subject macromolecules in implementations in which the monomer employed for the polymer backbone comprises a cyclic carbonate bearing one or more protected guanidinium functional groups.

Figure 2:
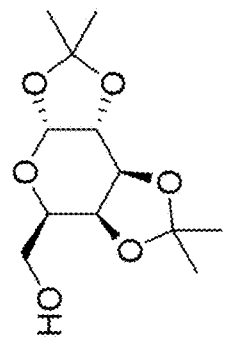
FIG. 2 illustrates chemical formulas of example, non-limiting protected monosaccharides that can be incorporated with one or more antimicrobial guanidinium macromolecules in accordance with one or more embodiments described herein.
Figure 2:
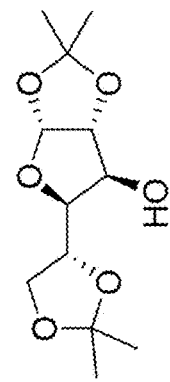
Figure 2:
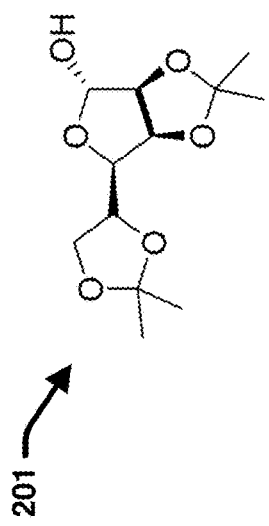
Figure 2:
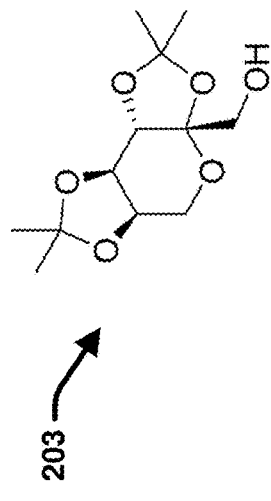

FIG. 2 illustrates chemical formulas of some example, non-limiting protected monosaccharides that can be incorporated with one or more antimicrobial guanidinium macromolecules as the targeting moiety R, or to initialize the targeting moiety R, in accordance with one or more embodiments described herein. The example protected monosaccharides 201, 202, 203 and 204 shown in FIG. 2 respectively include 2,3:5,6-Di-O-isopropylidene-a-D-mannofuranose, 1,2:3,4-Di-O-isopropylidene-alpha-D-galactopyranose, 2,3:4,5-Di-O-isopropylidene-beta-D-fructopyranose, and 1,2:5,6-Di-O-isopropylidene-alpha-D-glucofuranose. It should be appreciated that these protected sugars are merely exemplary and that other protected sugars can be employed as the targeting moiety R of the subject antimicrobial guanidinium based macromolecules.

With reference back to FIG. 1, in one or more embodiments, the polymer backbone can comprise polycarbonate. In other embodiments, the polymer backbone can comprise polylysine, polyionene, polyethylene imine and the like.

In one or more exemplary embodiments, the polymer backbone can be formed using a ring-opening polymerization of a cyclic carbonate monomer bearing one or more protected guanidinium functional groups. For example, in some implementations, the cyclic carbonate monomer can include methyltetrachloride (MTC) hydroxide (OH). (MTC-OH). With these embodiments, the subject antimicrobial guanidinium macromolecules can have a chemical structure characterized by Structure 100 shown in FIG. 1, and further characterized by Structure I below:

Structure I

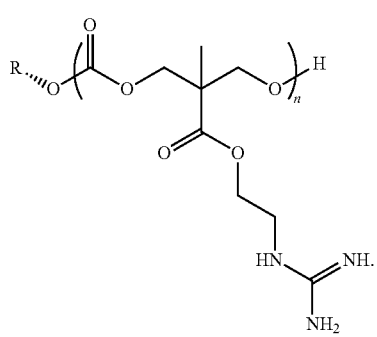

In Structure I, the guanidine-based antimicrobial moiety is connected to the polymer backbone via an ethyl spacer group S. However, the spacer group S of Structure 100 and the related structures described herein (e.g., Structure, Structure II, and the like), can vary. For example, in one or more additional embodiments, the spacer group S can include but is not limited to: a propyl group, a butyl group, a pentyl group, a cyclohexyl group, a phenyl group, or a benzyl group. In another embodiment, the spacer group S can include an isopropyl group. With this embodiment, the two guanidine-based antimicrobial moieties can be bound to the isopropyl group, supporting a Di-guanidinium functional group that extends from the polymer backbone.

Figure 3:
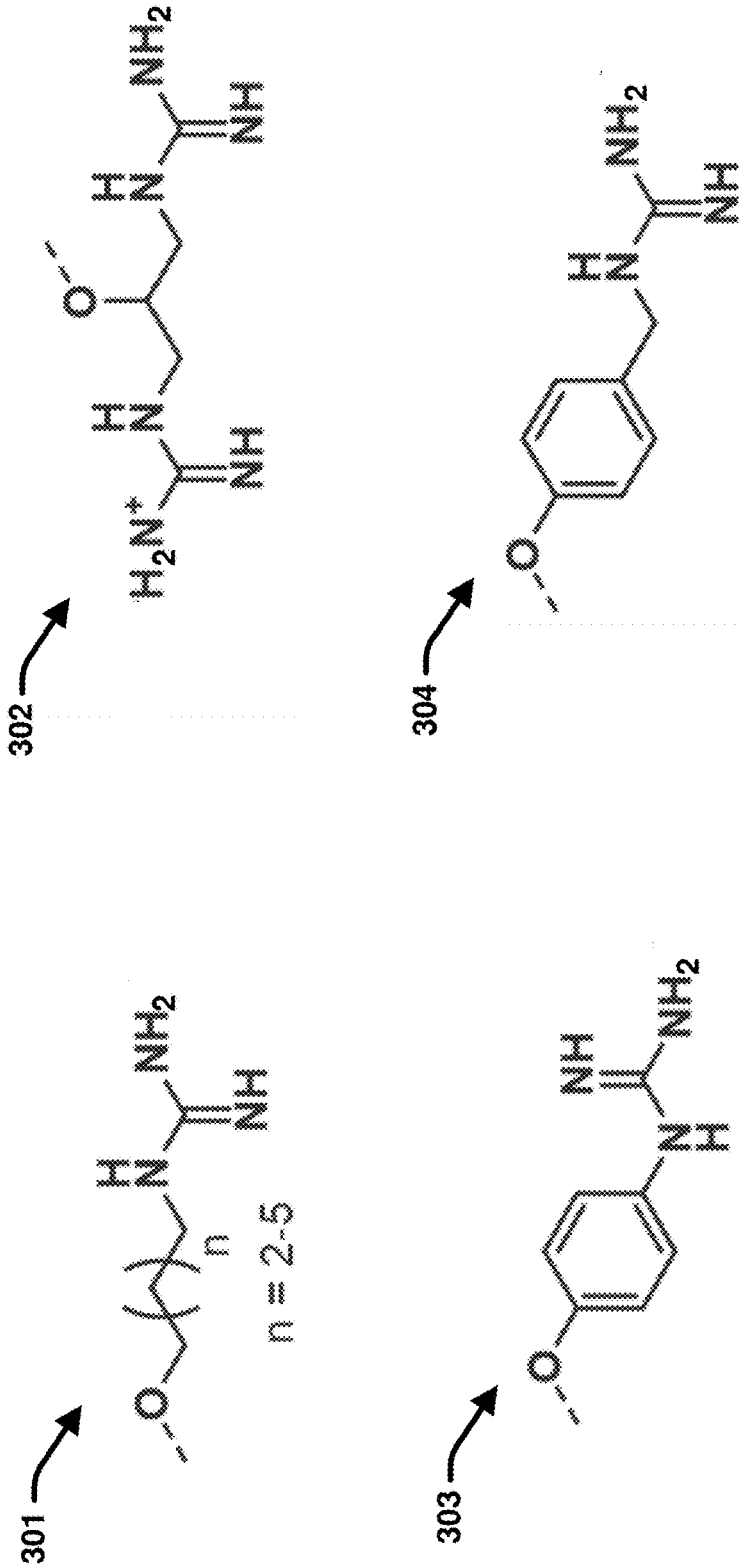
FIG. 3 illustrates chemical formulas of example, non-limiting guanidinium moieties comprising side-chains that can be incorporated as spacer groups in one or more antimicrobial guanidinium macromolecules in accordance with one or more embodiments described herein.

FIG. 3 illustrates chemical formulas of some example, non-limiting guanidinium moieties comprising side-chains that can be incorporated as the spacer group S of one or more antimicrobial guanidinium macromolecules in accordance with one or more embodiments described herein. The example guanidinium moieties are shown with various side chains bound to one or more guanidine compounds via single covalent bound to a nitrogen atom of the guanidinium moiety. For example, Formula 301 depicts a guanidinium moiety with either an ethyl, propyl, butyl, or pentyl side chain (e.g., as indicated by the number of carbons "n" being 2-5). Formula 302 depicts a Di-guanidinium moiety with an isopropyl side chain. Formula 303 depicts a guanidinium moiety with a phenyl side chain, and Formula 304 depicts a guanidinium moiety with a benzyl side chain. The oxygen atoms shown with dashed lines in Formulas 301, 302, 303 and 304 respectively represent the portion of the polymer backbone of the subject guanidinium-based macromolecules to which the side groups can connect (e.g., vi a single bond). It should be appreciated however that the manner in which the example side chains are bound to the polymer backbone and the atom or atoms to which the side chains are bound in the subject antimicrobial guanidinium-based macromolecules having Structure 100 (and variations thereof) can vary.

With reference to FIGS. 1-3, in view of various optional spacer group variations that can be employed for the spacer group S of Structure 100, in some embodiments, one or more antimicrobial guanidinium macromolecules described herein can be characterized by Structure 100 and further characterized by Structure II below:

Structure II

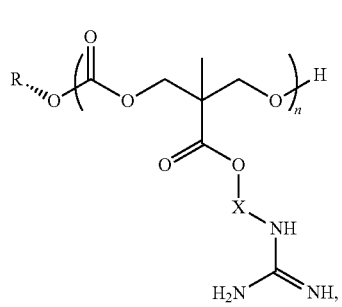

wherein X is a spacer group selected from a group consisting of: a propyl group, a butyl group, a pentyl group, a cyclohexyl group, a phenyl group, and a benzyl group. For example, in some embodiments, one or more antimicrobial guanidinium macromolecules described herein can be characterized by Structure 100 and further characterized by Structures III or IV below:

Structure III

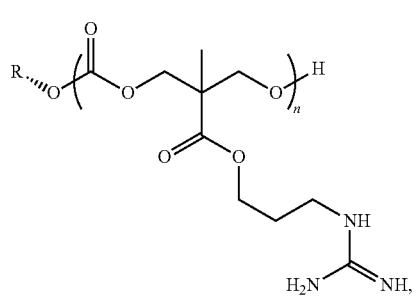

Structure IV

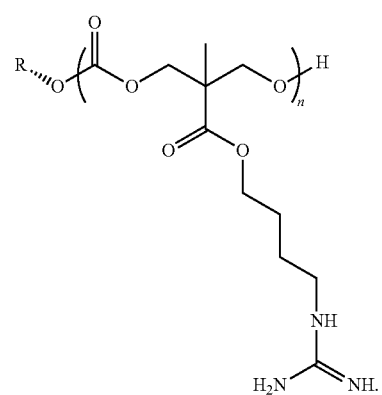

In Structures 100, I, II, III and IV, the quinine-based antimicrobial moiety is shown as a neutral structure, as represented by Formula I below.

Formula I

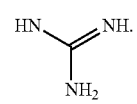

However, in some embodiments, the quinine-based antimicrobial moiety can be cationic in nature so as facilitate the charge neutralization with anionic surfaces of bacterial membranes, thereby facilitating translocation of the resulting nonpolar macromolecule through the bacterial membrane. In this regard, in some embodiments, the antimicrobial moiety can comprise a hydrosalt of a guanidinium functional group with a positively-charged protonated form of the guanidinium group that is ionically associated with a negatively-charged counterion. For example, in one or more implementations, such a hydrosalt of a quinidine group can be represented by Formula II below:

Formula II wherein X' is a negative-charged counterion. For example, in one or more implementations, the negative-charged counterion X' can comprise trifluoroacetic acid (TFA). With these implementations, the quinine-based antimicrobial moiety of the subject guanidinium based macromolecules can be a cationic guanidinium moiety represented by Formula III or Formula IV as follows:

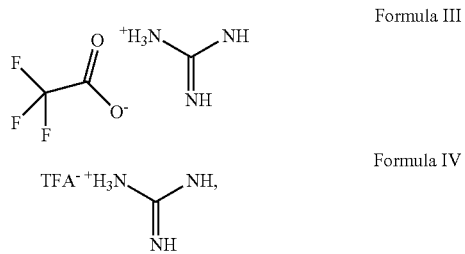

Formula III

Formula IV wherein TFA⁻ represents trifluoroacetic acid, the negatively charged counterion.

In various embodiments in which a neutral guanidinium moiety having chemical Formula I is described or depicted throughout the subject disclosure (e.g., in accordance with Structure 100 of FIG. 1 and Structures I, II III and IV above), the neutral guanidinium moiety can be interchanged for a cationic guanidinium moiety such as those represented by Formulas II, III, IV and the like, (and vice versa).

Figure 4A:
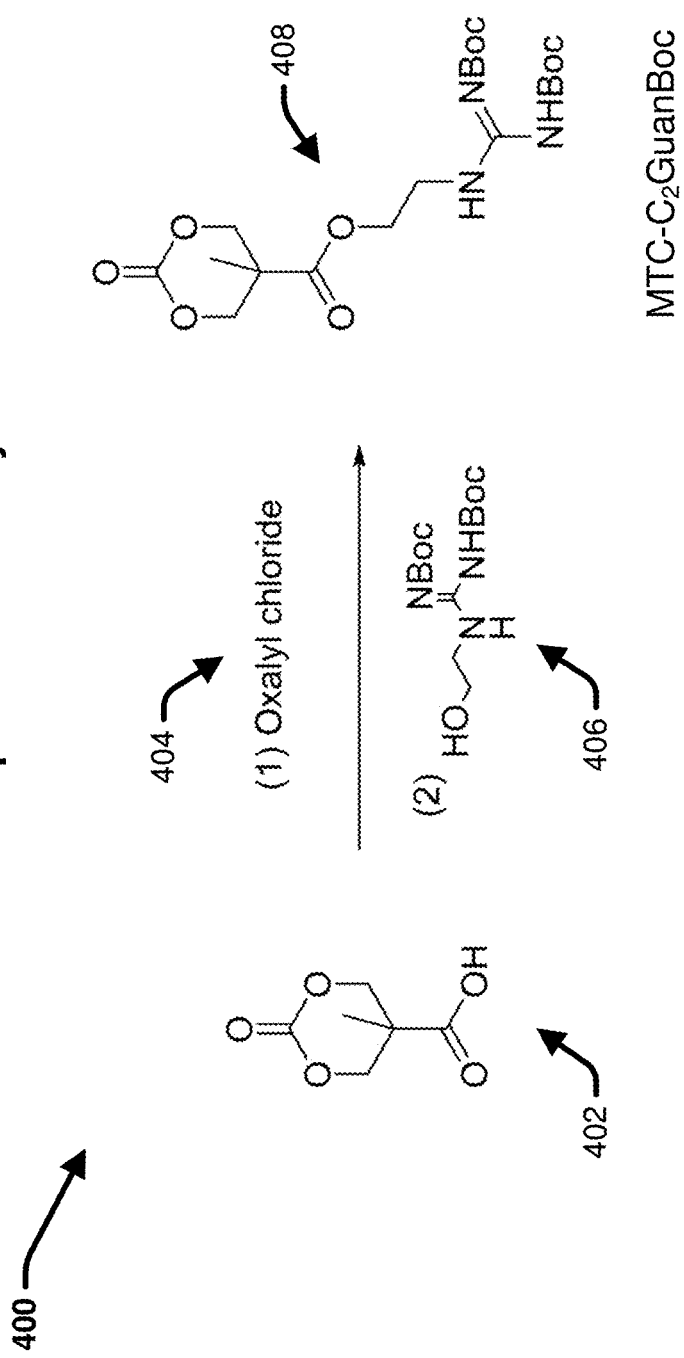
FIG. 4A illustrates a diagram of an example, non-limiting synthesis scheme that can facilitate generation of one or more guanidinium monomers in accordance with one or more embodiments described herein.

FIG. 4A illustrates a diagram of an example, non-limiting synthesis scheme 400 that can facilitate generation of one or more guanidinium functionalized monomers in accordance with one or more embodiments described herein. The one or more guanidinium functionalized monomers generated via synthesis scheme 400 can be further polymerized to generate one or more of antimicrobial guanidinium macromolecules in accordance with one or more embodiments described herein. For example, synthesis scheme 400 can be employed to produce one or more guanidinium functionalized monomers that can be used to generate one or more antimicrobial macromolecules characterized by Structure 100, Structure I and the like. Repetitive description of like elements employed in other embodiments described herein is omitted for sake of brevity.

In the embodiment shown, the resulting guanidinium functionalized monomer having Structure 408 is referred to herein as MTC-C₂GuanBoc. The guanidinium functionalized monomer MTC-C₂GuanBoc, comprises a cyclic carbonate (MTC) with a protected guanidinium functional moiety covalently bonded thereto via an ethyl spacer group. In this regard, the guanidinium moiety comprises two protecting tert-butyloxycarbonyl (tBoc or Boc) groups. The Boc groups can correspond to independent acid-liable protecting groups. Although the protecting groups of Structure 408 are Boc groups, other suitable protecting groups can be employed, such as but not limited to, benzyloxycarbonyl (Bnoc), and fluorenyloxycarbonyl (Fmoc).

In accordance with synthesis scheme 400 the MTC-C₂GuanBoc monomer can be prepared using by reacting one or more cyclic carbonates having Structure 402 with one or more protected guanidinium compounds having Structure 406 using a suitable amount of reagent oxalyl chloride 404. For example, in one implementation, synthesis scheme 400 was used to generate the Boc-protected guanidine-functionalized cyclic carbonate monomer (Boc-GC) having Structure 408 as follows. In a dry three-neck circular bottom flask (250 milliliters (mL)) equipped with a stir bar, MTC-OH (3.64 grams (g), or 22.75 millimoles (mmol)) was dissolved in dry tetrahydrofuran (THF). (50 mL) with 3-4 drops of dimethylformamide (DMF). A solution of oxalyl chloride (2.90 mL, 33.9 mmol) in dry THF (50 mL) was added dropwise to the above solution under an inert atmosphere, and the reaction continued for 1.0 hour until the addition of oxalyl chloride was completed. Then, a constant stream of nitrogen gas was bubbled through the reaction mixture for approximately 1.0 h to remove THF and other volatiles. The residue was dried under high vacuum to give a yellowish solid (i.e. 5-chlorocarboxy-5-methyl-1,3-dioxan-2-one intermediate). The solid was heated to 60 degrees Celsius (° C.) for 2-3 minutes to further remove any residual volatiles, and then re-dissolved in dry $CH_2Cl_2$ (50 mL) and cooled down to 0° C. via an ice bath under a nitrogen atmosphere. A mixture of Boc-Gua-OH (6.94 g, 21.0 mmol) and pyridine (1.84 mL, 22.9 mmol) dissolved in dry $CH_2Cl_2$ (50 mL) was then added dropwise over a duration of 30 minutes and allowed to stir at 0° C. for an additional 30 minutes before letting it react at ambient temperature overnight. After removal of the solvent, the crude product was subjected to purification by flash column chromatography using silica gel and a hexane-ethyl acetate solvent system as the eluent (gradient elution up to 50% volume ethyl acetate) to yield Boc-GC as a white powder (6.1 g, 88% yield). The results of a proton nuclear magnetic resonance ($^1$H NMR) study of the Boc-GC at 400 megahertz (MHz), in deuterated chloroform (CDCl₃) at 22 degrees Celsius (° C.), were as follows: δ 11.47 (s, 1H, —NH—), 8.33 (s, 1H, —NH—), 4.65 (d, 2H, —CH₂OCOO—), 4.20 (m, 4H, —CH₂OCOO— and —OCH₂—), 3.42 (dd, 2H, —CH₂N—), 1.62-1.70 (m, 4H, —CH₂—), 1.47 (s, 18H, Boc-CH₃), 1.31 (s, 3H, —CH₃).

In another implementation, synthesis scheme 400 was used to generate another guanidinium functionalized monomer Boc-protected guanylated butanol (Boc-Gua-OH) as follows, 1,3-Bis(tert-butoxycarbonyl)-2-methyl-2-thiopseudourea (6.6 g, 23.2 mmol) was dissolved in 20 mL of dry $CH_2Cl_2$, and the solution was added to the mixture of 4-amino-1-butanol (4.2 mL, 44.6 mmol) and N,N-diisopropylethylamine (12.0 mL, 68.8 mmol). The reaction mixture was left to stir overnight at room temperature. Upon reaction completion, a constant stream of nitrogen gas was bubbled through the reaction mixture for approximately 1.0 hour to purge the gaseous by-product. MeSH. After the removal of residual solvent in vacuo, the crude product was purified by flash column chromatography using silica gel and a hexane-ethyl acetate solvent system as the eluent (gradient elution up to 50% vol, ethyl acetate) to yield the Boc-protected guanylated butanol (Boc-Gua-OH) as a white powder (7.0 g, 95% yield). The results of a $^1$H NMR (400 MHz, CDCl$_3$, 22° C.) were as follows: δ 11.48 (s, 1H, —NH—), 8.42 (s, 1H, —NH—), 3.70 (dd, 2H, HOCH$_2$—), 3.46 (dd, 2H, —CH$_2$NH—), 1.65 (m, 4H, —CH$_2$—), 1.50 (d, 18H, Boc-CH$_3$).

While one or more particular reactants (e.g., cyclic carbonate having Structure 402, protected guanidinium compounds having Structure 406, etc.), reagents, and/or solvents are depicted; additional embodiments of synthesis scheme 400 are also envisaged. For example, the principal mechanisms of synthesis scheme 400 can be applied to various carbonate based homopolymers, polylysine based homopolymers, polyionene based homopolymers, polyethylene based homopolymers, and various guanidinium compounds (e.g., comprising one or more guanidinium moieties having various alternative side chains, such as those described with reference to FIG. 3 and the like), in accordance with the various features described herein.

Figure 4B:
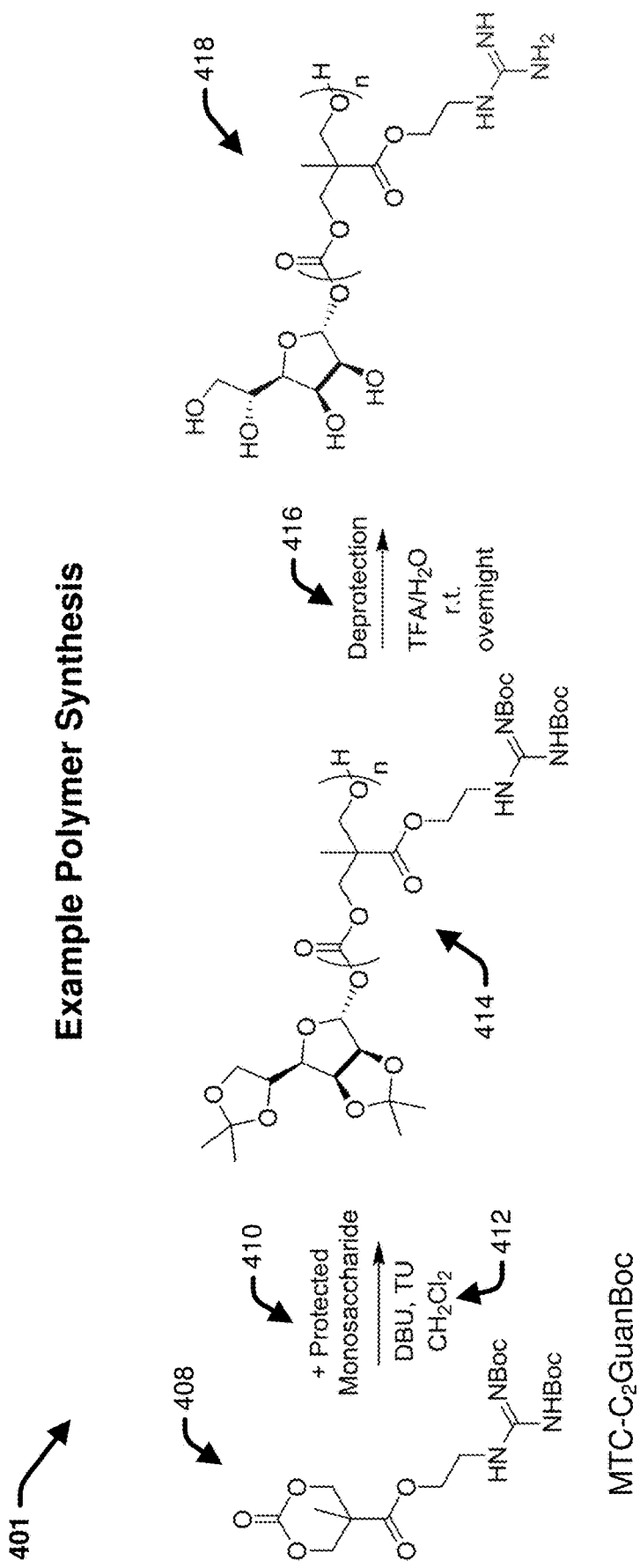
FIG. 4B illustrates a diagram of an example, non-limiting synthesis scheme that can facilitate generation of one or more guanidinium polymers in accordance with one or more embodiments described herein.

FIG. 4B illustrates a diagram of an example, non-limiting synthesis scheme 401 that can facilitate generation of one or more antimicrobial guanidinium macromolecules in accordance with one or more embodiments described herein. In this regard, synthesis scheme 401 can be employed to produce one or more antimicrobial polymers characterized by Structure 100. Structure I and the like. Repetitive description of like elements employed in other embodiments described herein is omitted for sake of brevity.

Synthesis scheme 401 can be employed to install various small molecule monosaccharides onto a guanidinium functionalized polymer backbone using various protected monosaccharides as the initiator 410. For example, in some embodiments, the protected monosaccharide can be D-mannose diacetonide. Other suitable protected monosaccharides for the initiator 410 can include but are not limited to, diacetone-D-galactose, diacetone-D-glucose, and diacetone-D-fructose. Synthesis scheme 401 particularly exemplifies the generation of one or more antimicrobial guanidinium macromolecules prepared by organocatalyzed ring opening polymerization (OROP) of one or more guanidinium functionalized monomers MTC-C$_2$GuanBoc having Structure 408. In accordance with synthesis scheme 401, the OROP of MTC-C$_2$GuanBoc can be performed using a protected monosaccharide as the initiator 410 (and corresponding targeting moiety), and one or more reagents 412. For example, the reagents 412 can include but are not limited to, an organo-catalyst (e.g. 1,8-Diazabicyclol[5,4,0]-undec-7-ene (DBU), N-(3,5-trifluoromethyl)phenyl-N-cyclohexylthiourea (TU), or DBU/TU), a solvent (e.g., methylene chloride (CH$_2$CL$_2$)), and optionally, an accelerator.

The OROP of the one or more guanidinium functionalized monomers MTC-C$_2$GuanBoc produces an intermediate protected homopolymer having Structure 414. The intermediate protected homopolymer comprises a polymer backbone consisting of a plurality of repeat carbonate units respectively comprising protected guanidinium groups extending therefrom (e.g., wherein the number of repeat units corresponds to the variable "n" of Structure 100 and the like). In various embodiments, the number of repeat units is between 5 and 65, however it should be appreciated that any number of repeat units greater than one and less than one thousand are envisioned. In particular, due to the exquisite level of control of OROP, synthesis scheme 401 can be employed to synthesize protected homopolymer having Structures 414 (and the like) to desired repeat unit lengths based on the initial monomer to initiator (e.g., MTC-C$_2$GuanBoc to protected monosaccharide) feed ratio. The intermediate protected homopolymer further comprises a protected sugar group covalently bonded to a peripheral end of the polymer backbone.

Subsequent deprotection 416 of the intermediate protected homopolymer forms a resultant antimicrobial polymer having Structure 418. The deprotection of the protected homopolymer at 416 can be performed using trifluoroacetic acid (TFA), or another suitable protic acid. The resultant antimicrobial polymer comprises one or more guanidinium functional groups respectively attached to a polymer backbone and a monosaccharide targeting moiety that extends from a peripheral end of the polymer backbone. In this regard, the chemical Structure 418 of the resultant antimicrobial guanidinium macromolecule generated via synthesis scheme 401 corresponds to Structure 100 and Structure I, wherein the antimicrobial moiety R comprises a single monosaccharide unit, and the polymer backbone comprises a plurality of guanidinium functionalized carbonate units respectively attached thereto via an ethyl spacer group S.

In various exemplary implementations, synthesis scheme 401 was performed separately using four different protected sugars, including D-mannose diacetonide, diacetone-D-galactose, diacetone-D-glucose, and diacetone-D-fructose, to generate four different intermediate protected homopolymers (e.g., having Structure 414 or the like) and subsequent protected antimicrobial macromolecules (e.g., having Structure 418 or the like) with different sugar targeting moieties R. The protected polymers are respectively referred to herein as mannose-C$_2$GuanBoc, galactose-C$_2$GuanBoc, glucose-C$_2$GuanBoc. and fructose-C$_2$GuanBoc. The respective protected polymers mannose-C$_2$GuanBoc, galactose-C$_2$GuanBoc, glucose-C$_2$GuanBoc. and fructose-C$_2$GuanBoc were characterized by comparing various integrated intensities of the $^1$H resonances from protons of the sugar initiators relative to the backbone and pendant groups of the Boc protected guanidine monomer. The protected polymers mannose-C$_2$GuanBoc, and galactose-C$_2$GuanBoc, glucose-C$_2$GuanBoc exhibited narrow molecular weight distribution with a polydispersity index ranging between 1.16 and 1.20 based on gel permeation chromatography prior to post functionalization deprotection 416.

For example, in one or more embodiments, mannose-C$_2$GuanBoc was prepared in accordance synthesis scheme 401 and the following protocol. Initially, the OROP of MTC-C$_2$GuanBoc with D-mannose diacetonide was performed at a molar ratio of 25:1. In this regard, mannose-C$_2$GuanBoc was prepared by dissolving D-mannose diacetonide (e.g., at 12 milligrams (mg), or 0.045 millimoles (mmol)) together with TU (e.g., at 20 mg, or 0.056 mmol) and MTC-C$_2$GuanBoc (e.g., at 0.5 grams (g), or 1.12 mmol) in 2.0 milliliters (ml) of CH$_2$Cl$_2$. Upon complete dissolution. DBU (8.4 microliters (μL), 0.056 mmol) was introduced and the solution was stirred at room temperature for about 3.5 hours, followed by addition of benzoic acid (e.g., at 30.0 mg) for quenching. The example mannose-C$_2$GuanBoc was then purified by precipitation twice in hexane at room temperature.

Initiations of OROP via other acetonide protected monosaccharides, including diacetone-D-galactose, diacetone-D-glucose, and diacetone-D-fructosc with MTC-C$_2$GuanBoc were conducted similarly to the above protocol to generate galactose-C$_2$GuanBoc, glucose-C$_2$GuanBoc, and fructose-C$_2$GuanBoc, and the resulting polymers were purified by precipitation in hexane.

The example mannose-C$_2$GuanBoc polymer prepared in accordance with synthesis scheme 401 and the above noted protocol demonstrated a yield of 0.41 grams (g) or (81%).

The results of a proton nuclear magnetic resonance ($^1$H NMR) study at 400 megahertz (MHz), in deuterated chloroform (CDCl$_3$) at 22 degrees Celsius (° C.), provided the following: 11.70-11.33 (m, 18H, [—NHCOOC(CH$_3$)$_3$]), 9.18-8.40 (m, 18H, —CH$_2$NHC—), 6.05-4.74 (m, 3H, protons from diacetone-D-mannose), 4.46-4.10 (m, 110H, —OC$_2$H$_4$OCH—, —COOCH$_2$CH$_2$— and proton from diacetone-D-mannose), 3.88-3.62 (m, 36H, —COOCH$_2$CH$_2$—), 1.75-1.65 (m, 12H, [—C(CH$_3$)$_2$]$_2$, 1.55-1.41 (m, 342H, [—COOC(CH$_3$)$_3$]$_2$), 1.29-1.05 (m, 57H, —CH$_3$). A disparity (Đ) of Đ=1.17 was observed.

The example galactose-C$_2$GuanBoc polymer prepared in accordance with synthesis scheme 401 and the above noted protocol has the following chemical properties: $^1$H NMR (400 MHz, CDCl$_3$, 22° C.): 12.29-10.68 (m, 19H [—NHCOOC(CH$_3$)$_3$]), 8.96-8.33 (m, 19H, —CH$_2$NHC—), 6.02-4.73 (m, 3H, protons from Diacetone-D-galactose), 4.50-3.91 (m, 118H, —OC$_2$H$_4$OCH—, —COOCH$_2$CH$_2$— and protons from Diacetone-D-galactose), 3.76-3.65 (m, 38H, —COOCH$_2$CH$_2$—), 1.76-1.60 (m, 12H, [—C(CH$_3$)$_2$]$_2$, 1.55-1.39 (m, 342H, [—COOC(CH$_3$)$_3$]$_2$), 1.29-1.17 (m, 54H, —CH$_3$), Đ=1.16.

The example glucose-C$_2$GuanBoc polymer prepared in accordance with synthesis scheme 401 and the above noted protocol has the following chemical properties: $^1$H NMR (400 MHz, CDCl$_3$, 22° C.): 11.70-11.33 (m, 16H [—NHCOOC(CH$_3$)$_3$]), 9.18-8.40 (m, 16H, —CH$_2$NHC—), 6.03-4.77 (m, 3H, protons from Diacetone-D-glucose), 4.46-4.10 (m, 100H, —OC$_2$H$_4$OCH—, —COOCH$_2$CH$_2$— and proton from Diacetone-D-glucose), 3.88-3.62 (m, 32H, —COOCH$_2$CH$_2$—), 1.75-1.65 (m, 12H, [—C(CH$_3$)$_2$]$_2$, 1.55-1.41 (m, 288H, [—COOC(CH$_3$)$_3$]$_2$), 1.29-1.05 (m, 48H, —CH$_3$). Đ=1.20.

The example fructose-C$_2$GuanBoc polymer prepared in accordance with synthesis scheme 401 and the above noted protocol has the following chemical properties: $^1$H NMR (400 MHz. CDCl$_3$, 22° C.): 11.10-10.82 (m, 17H [—NHCOOC(CH$_3$)$_3$]), 8.66-8.30 (m, 17H, —CH$_2$NHC—), 6.13-4.68 (m, 3H, protons from diacetone-D-fructose), 4.55-3.86 (m, 106H, —OC$_2$H$_4$OCH—, —COOCH$_2$CH$_2$— and protons from diacetone-D-fructose), 3.73-3.68 (m, 34H, —COOCH$_2$CH$_2$—), 1.70-1.61 (m, 12H, [—C(CH$_3$)$_2$]$_2$, 1.53-1.34 (m, 306H, [—COOC(CH$_3$)$_3$]$_2$), 1.30-1.16 (m, 51H, —CH$_3$). Đ=1.16.

Synthesis scheme 401 was further continued for mannose-C$_2$GuanBoc, galactose-C$_2$GuanBoc, glucose-C$_2$GuanBoc and fructose-C$_2$GuanBoc, wherein both the acetonide and Boc protecting groups were removed in a one-step reaction under acidic conditions in accordance with deprotection 416. In this regard, separately, the respective protected polymers were charged in a glass vial with 1.0 mL of CH$_2$Cl$_2$ equipped with a stir bar, with the addition of TFA (e.g., 2.0 ml) and H$_2$O (0.2 ml) under constant stirring at room temperature for 18 hours. The solvent of the reaction mixture was subsequently removed in vacuo, and the residue was dialyzed against acetonitrile/isopropanol (1:1 volume of solute to volume of solution (v/v)) in a dialysis bag with molecular weight cut-off (MWCO) of 1000 Da (Spectra/Por 7, Spectrum Laboratories Inc.) for 24 hours. Finally, the solvent within the dialysis bag was removed under vacuum.

Because the boc protecting groups can easily be removed under TFA conditions, the deprotection reactions were highly efficient where full deprotection was observed. The catalytic addition of a drop of water to the reaction environment allowed for mild and effective removal of the acetonide protecting group from the sugar initiator. (e.g., as determined by $^1$H NMR spectroscopy). To enhance clarity, the resultant deprotected polymers having Structure 418 and prepared in accordance with synthesis scheme 401 and the protocol described above, are referred to herein according to their respective sugar initiators, as well as the degree of polymerization after deprotection and dialysis. In this regard, the resultant antimicrobial polymers (having Structure 418 or the like) are respectively referred to herein as mannose_16, galactose_18, glucose_17, and fructose_16. For example, mannose_16 denotes a homopolymer containing 16 repeating units of deprotected guanidine side groups with a mannose furanose initiator, while fructose_16 denotes a polymer of similar chain length containing a fructose initiator, and so on.

The resultant mannose_16 obtained was a white sticky polymer at about an 80% yield or more. The $^1$H NMR performed at 400 MHz, in dimethyl sulfoxide (DMSO$_d$) at 22° C. demonstrated the following chemical properties: 7.73-7.00 (m, 64H, —CH$_2$NHC=NHNH$_2$), 5.20-5.04 (m, 2H, anomeric protons from mannose furanose), 4.79-4.16 (m, 68H, —OC$_2$H$_4$OCH— and 4 protons from mannose furanose), 4.15-4.03 (m, 32H, —COOCH$_2$CH$_2$—), 1.37-1.06 (m, 48H, —CH$_3$). A yield of greater than 85% was obtained for example galactose_18. The $^1$H NMR for galactose_18 (also performed at 400 MHz DMSO$_d$ at 22° C.) demonstrated the following chemical properties: 7.75-6.68 (m, 72H, —CH$_2$NHC=NHNH$_2$), 5.12-5.05 (m, 2H, anomeric protons from galactose), 4.64-4.16 (m, 76H, —OC$_2$H$_4$OCH— and 4 protons from galactose), 4.15-4.03 (m, 36H, —COOCH$_2$CH$_2$—), 3.56-3.52 (m, 2H, H$_\beta$ of galactose), 3.50-3.39 (m, 36H, —COOCH$_2$CH$_2$—), 1.26-1.08 (m, 54H, —CH$_3$). The example, antimicrobial polymer glucose_17 has the following properties: (>80% yield). $^1$H NMR (400 MHz, DMSO$_d$, 22° C.): 7.67-6.89 (m, 64H, —CH$_2$NHC=NHNH$_2$), 5.15-5.07 (m, 2H, anomeric protons from glucose), 4.48-4.17 (m, 72H, —OC$_2$H$_4$OCH— and 4 protons from glucose), 4.16-4.00 (m, 34H, —COOCH$_2$CH$_2$—), 1.29-1.18 (m, 51H, —CH$_3$). The example fructose_16 has the following properties: (>85% yield). $^1$H NMR (400 MHz, DMSO$_d$, 22° C.): 7.69-6.85 (m, 64H, —CH$_2$NHC=NHNH$_2$), 5.15-5.08 (m, 2H, anomeric protons from galactose), 4.97-4.16 (m, 68H, —OC$_2$H$_4$OCH— and 4 protons from galactose), 4.14-4.02 (m, 32H, —COOCH$_2$CH$_2$—), 3.59-3.51 (m, 2H, H$_\beta$ of fructose), 3.49-3.38 (m, 32H, —COOCH$_2$CH$_2$—), 1.29-1.06 (m, 48H, —CH$_3$).

The guanidinium-based macromolecules disclosed herein, including guanidinium-based macromolecules having Structure 100, Structure I, Structure II, Structure III, Structure IV, Structure 418, mannose_16, galactose_18, glucose_17, fructose_16, the like, have demonstrated strong efficacy as antimicrobial agents against both Gram-negative and Gram-positive microbes, including MDR microbes, such as but not limited to: *K. pneumoniae. A. baumannii, Escherichia coli* (*E. coli*), *Staphylococcus aureus* (*S. aureus*), methicillin-resistant *S. aureus* (MRSA), and *Pseudomonas aeruginosa* (*P. aeruginosa*). The subject guanidinium-based macromolecules have also demonstrated high efficacy (e.g., a 100% bacterial growth inhibition rate) at relatively low effective dose (ED) amounts (e.g., an ED$_{50}$ less than 7.0 milligrams/kilogram (mg/kg) and an ED$_{95}$ less than 21.0 mg/kg), no (or extremely low) toxicity (e.g., as demonstrated via a RBC viability level greater than 95% at an effective dose), and strong immunity to development of antimicrobial resistance.

In this regard, the efficacy, toxicity and antimicrobial resistance development characteristics of the subject guanidinium-based macromolecules (e.g., particularly mannose_16 and glucose_17) was tested in vitro and in vivo (e.g., in a mouse model), against clinically isolated bacterial strains, including MDR *K. pneumoniae, E. coli, A. baumannii*, and MRSA strains. To facilitate comparison, an antimicrobial guanidinium-based macromolecule without a sugar functional group (identified herein as Dp20), as well as strong antibiotics (including imipenem, vancomycin, ceftriaxone, and gentamycin), were also tested against the clinically isolated pathogens. The MDR clinical isolates were obtained from patients' blood and phlegm. All isolates were identified by routine laboratory methods and stored in 20% (v/v) glycerol at 80☐. The in vitro tests are described with reference to FIGS. 5-8, and the in vivo tests are described with reference to FIGS. 9-11.

FIGS. 5 and 6 respectively illustrate the MICs of mannose_16 and glucose_17 relative to Dp20 and antibiotics (ceftriaxone, gentamycin, imipenem, and vancomycin) against the clinical isolates mentioned above. The MICs of mannose_16, glucose_17, Dp20 and the respective antibiotics against the clinical isolates were measured via the broth microdilution method. In accordance with the broth microdilution method, MDR microbes including one or more strains of *K. pneumoniae. E. coli. A. baumannii*, and MRSA were harvested in midexponential growth phase after grown overnight in Mueller-Hinton (MH) agar plates at 37'. The antimicrobial agents were prepared in Mueller Hinton broth (MHB) at various concentrations. The bacteria suspensions were then diluted with phosphate-buffer saline (PBS), with a potential of Hydrogen (PH) of 7.4 to adjust the turbidity approximately to the Standard McFarland 0.6, which corresponds to the concentration of $1 \times 10^8$ colony-forming unit (CFU) per mL (CFU/mL, after which the bacteria suspension was further diluted by 100-fold with MHB ($1 \times 10^6$ CFU/mL). Subsequently, equal volumes (100 μL) of bacterial suspension and agent solution prepared previously were mixed in each well of a 96-well plate and incubated for 18 hours at 37° C. Broth containing bacteria alone was employed as the negative control, and each MIC was tested in triplicate. The results are presented in FIGS. 5 and 6.

In this regard. FIG. 5 presents an example, non-limiting table 500 providing the cumulative distribution of MIC values (in μg/mL) for Dp20, mannose_16, glucose_17, ceftriaxone, gentamycin, and imipenem against 10 clinically isolated MDR *A. baumannii* strains. As reported in FIG. 5, the MIC values represent the lowest concentration of the tested antimicrobial agents at which no visible turbidity was observed with unaided eyes, or 100% bacterial growth inhibition. The MIC values measured range from 1.0 (μg/mL) to 512 μg/mL or greater (exponentially increased) and are presented at the top of chart 500 along the x-axis. The values provided within the respective cells of table 500 and correspond to different percentages of bacterial strains observed at the respective MIC values. In this regard, a value of 100 for Dp20 corresponds to 100% bacterial strains (e.g., 10 out of 10 strains) which have the particular MIC value (64 μg/mL) or below, a value of 90 corresponds to 90% bacterial strains (e.g., 9 out of 10 strains) which have the particular MIC value (32 μg/mL) or below, a value of 60 corresponds to 60% bacterial strains (e.g., 6 out of 10 strains) which have the particular MIC value (16 μg/mL), and so on.

As shown in table 500, to inhibit the growth of 10 MDR *A. baumannii* strains, 64.0, 16.0 and 32.0 μg/mL is needed for DP20, mannose_16 and glucose_17, respectively. Accordingly, antimicrobial guanidinium-based polymers initiated from either mannose or glucose have shown substantially higher activity than guanidinium polymers without the carbohydrate targeting moiety and the antibiotic controls.

FIG. 6 presents an example, non-limiting table 600 comparing the MIC values (in micrograms (μg)/mL) of the tested antimicrobial agents against different types and strains of clinically isolated MDR bacteria. As reported in FIG. 6, the MIC values represent the lowest concentration of the tested antimicrobial agents at which no visible turbidity was observed with unaided eyes, or 100% bacterial growth inhibition. As shown in table 600, mannose_16 and glucose_17 demonstrated high efficacy against each of the tested bacterial strains with MIC values ranging from only 4.0 μg/mL to 32.0 μg/mL. In this regard, both mannose_16 and glucose_17 demonstrated broad-spectrum efficacy against Gram-negative and Gram-positive strains, whereas imipenem only demonstrated efficacy against the Gram-negative strains (e.g., the *K. pneumoniae* (KP), *E. coli* (EC), and *A. baumannii* (AB) strains), and vancomycin only demonstrated efficacy Gram-positive strains (e.g., the methicillin-resistant *S. aureus* (MSRA) strains). In addition, the MIC values for mannose_16 and glucose_17 are substantially lower than those of Dp20 with respect to each of the different bacterial strains. Further, the MIC values for mannose_16 and glucose_17 are substantially lower than the MIC values for imipenem with respect to strains KP7958, KP9170, AB4123 and AB10361.

Figure 7:
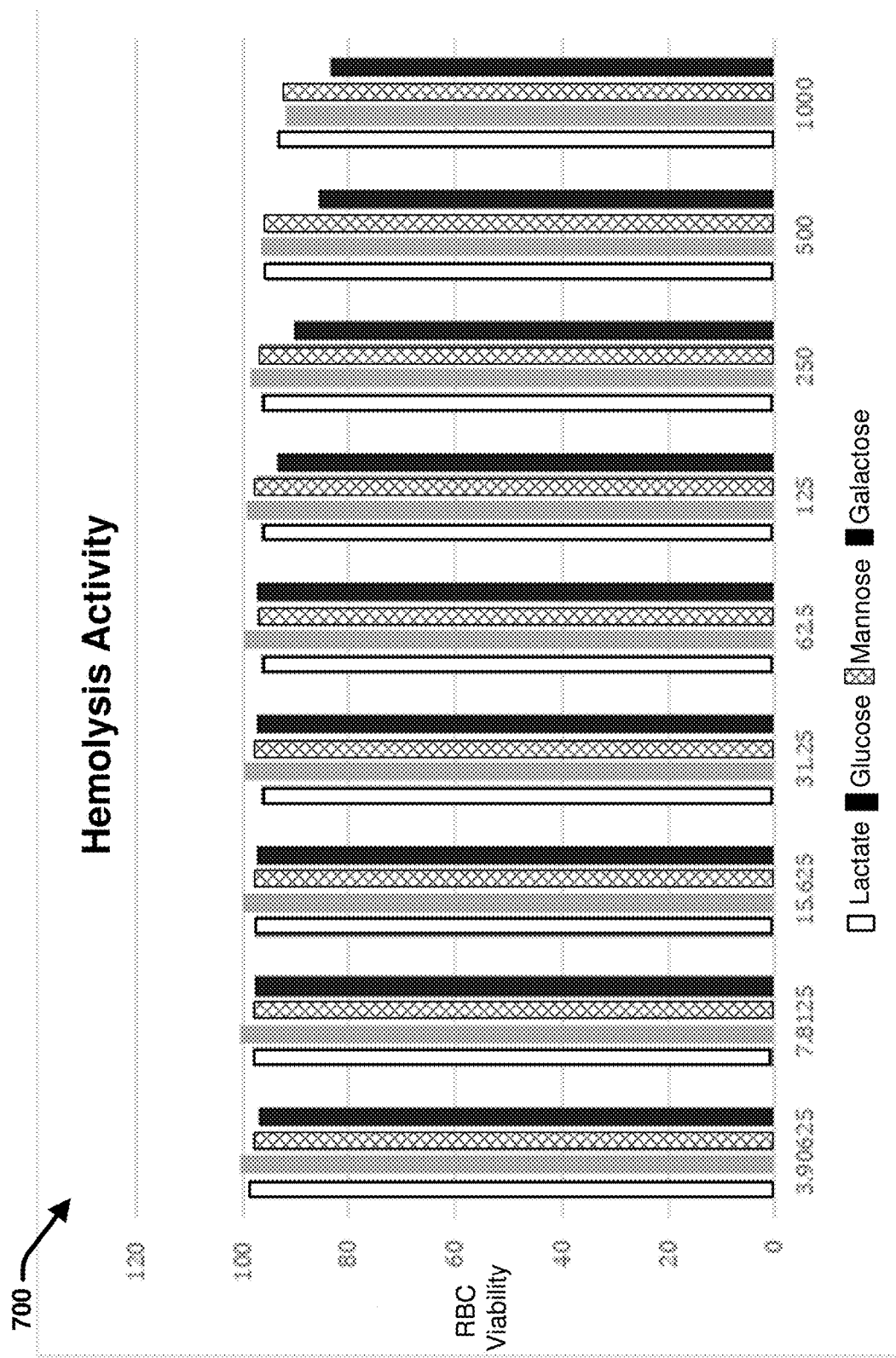
FIG. 7 illustrates an example, non-limiting graph that depicts hemolysis activity of one or more antimicrobial guanidinium macromolecules in accordance with one or more embodiments described herein.

FIG. 7 illustrates an example, non-limiting graph 700 that depicts hemolysis activity of one or more guanidinium macromolecules in accordance with one or more embodiments described herein. In this regard, the RBC hemolytic activity of guanidinium-based macromolecules having structure 100 with various sugar moieties (lactate, glucose, mannose and galactose) as the targeting moiety R were tested at various concentrations (measured in μg/mL). As shown in FIG. 7, at polymer concentrations within the therapeutic dose (e.g., 64 μg/mL or less), no hemolytic activity (e.g., as shown via a RBC viability level of 100%) was demonstrated by the glucose functionalized guanidinium based polymers and extremely low hemolytic activity was demonstrated by the polymers including the other sugar moieties (e.g., as shown via the RBC viability level at about 95% or greater). This low hemolytic activity was further demonstrated for each of the different sugar moiety based polymers far past the therapeutic dose. For example, even at concentrations up to 1000 μg/mL, the respective polymers demonstrated RBC viability greater than 80%. Accordingly, the disclosed guanidinium macromolecules with different sugar targeting moieties are thus highly selective towards bacterial cells (e.g., as opposed to RBCs) and nontoxic even at the high polymer concentrations.

Figure 8:
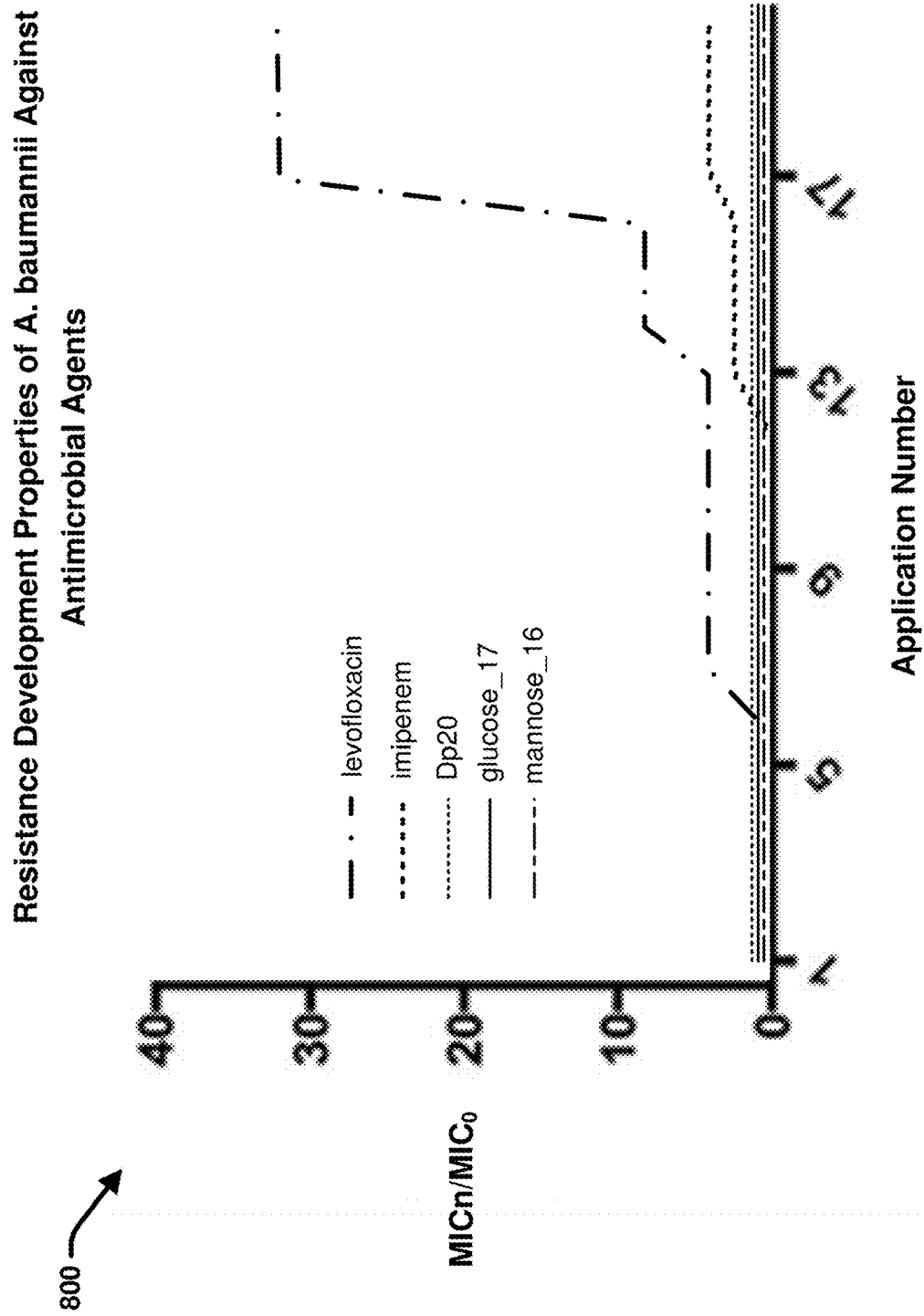
FIG. 8 illustrates an example, non-limiting graph that demonstrates the robustness of one or more antimicrobial guanidinium macromolecules against inducing antimicrobial agent resistance in accordance with one or more embodiments described herein.

FIG. 8 illustrates an example, non-limiting graph 800 that demonstrates the robustness of one or more guanidinium macromolecules against bacteria resistance development in accordance with one or more embodiments described herein. In this regard, *A. baumannii* 4123 was employed to study the propensity to develop resistance against mannose_16 and glucose_17, as well as Dp20, imipenem and levofloxacin for comparison. To test bacterial resistance and resistance prevention, a sub-lethal dose (so as to not kill all bacteria) of the respective antimicrobials was repeatedly applied to *A. baumannii* samples for 24 hours at each passage, wherein the bacteria were allowed to replicate and/or mutate. The MIC values of the respective antimicrobials were then measured after each repetition to monitor MIC changes. An increase in MIC value indicates development of resistance in the bacteria. In particular, samples of *A. baumannii* bacteria were first exposed to the respective antimicrobials (e.g., mannose_16 and glucose_17, Dp20, imipenem and levofloxacin) for the determination of MICs as described above. Subsequently, 50.0 µL of bacteria from wells of 0.5×MIC were harvested and grown overnight, and then subjected to MIC determinations for up to 20 similar serial passages (e.g., single applications once a day for 20 days).

The development of resistance to the antimicrobial agents in A. baumannii was monitored by recording the changes in the MIC as shown via graph 800. The three horizontal lines at the bottom of graph 800 respectively correspond to Dp20, glucose_17 and mannose_16. As shown via graph 800, repeated use of the sugar-functionalized polymers glucose_17 and mannose_16, (as well as Dp20), did not cause resistance in A. baumannii 4123, while the bacteria with multiple treatments with imipenem or levofloxacin developed significant resistance. The respective lines at the bottom of graph 800 for Dp20, glucose_17 and mannose_16 are shown slightly above the zero MIC value for illustrative purposes. However, in practice each of the measured MIC values for Dp20, glucose_17 and mannose_16 remained constant (i.e. $MIC_n/MIC_0=1$, where $MIC_n$ represents MIC at n passage, and $MIC_0$ represents MIC at 0 passage).

In addition to the in vitro studies discussed above, FIGS. 9-11 demonstrate the antimicrobial efficacy of the subject guanidinium-based macromolecules (e.g., particularly mannose_16 and glucose_17) as tested relative to Dp20 and imipenem in a mouse model (e.g., in vivo). In this regard, immunosuppressed mice were used for the following in vivo studies. Immunosuppression was induced by intraperitoneal injection of 200 mg/kg cyclophosphamide 4 days prior to infection. The mice were anesthetized by intraperitoneal injection of 1% pentobarbital (40 mg/kg, sigma). The mice were then infected with A. baumannii 4123 to determine the minimum lethal dose for subsequent effective dose and efficacy testing. Briefly, overnight cultures of A. baumannii 4123 were harvested and suspended in phosphate-buffered saline (PBS). Subsequently, the cyclophosphamide-pretreated mice were injected with 0.3 mL of the bacterial suspension at designated doses (e.g., $1.0\times10^8$, $2.5\times10^8$, $5\times10^8$, $1.0\times10^9$, $2.0\times10^9$ CFU/mL, six mice per group) via the tail vein. The minimum lethal dose, the lowest concentration sufficient to cause 100% mortality, was determined from the survival rate of mice at 48 hours post-infection by the BLISS method.

The effective doses $ED_{50}$, (the effective dose that cures 50% infected mice), and $ED_{95}$. (the effective dose that cures 95% infected mice), of mannose_16 and glucose_17, and Dp20 and imipenem for comparison, were tested using an A. baumannii 4123-caused bacteremia infection mouse model as follows. Firstly, a bacterial suspension with the minimum lethal dose (0.3 mL) was introduced to the above described cyclophosphamide-pretreated mice via the tail vein. The antimicrobial agents (e.g., mannose_16, glucose_17, Dp20 and imipenem) were then respectively administered to different groups of mice (six mice per group) intraperitoneally, 1.0 and 6.0 hours after infection at designated doses (e.g., 1.0, 2.5, 5.0, 7.5, 10.0, 15.0, 20.0 mg/kg for mannose_16, glucose_17. Dp20 and imipenem, 0.2 mL/20 g). The number of surviving mice in each group was recorded for 7.0 days to estimate $ED_{50}$ and $ED_{95}$ via the BLISS method. The results are provided in FIG. 9.

Figure 9:
FIG. 9 presents an example, non-limiting table demonstrating the effective dose evaluation of various antimicrobials, including the subject antimicrobial guanidinium macromolecules, against *A. baumannii* in a blood infected mouse model, accordance with one or more embodiments described herein.

In particular, FIG. 9 presents an example, non-limiting table 900 demonstrating the results of the above described effective dose evaluation of various antimicrobials, including the subject guanidinium-based macromolecules, against A. baumannii 4123 in the blood infected mouse model, in accordance with one or more embodiments described herein. As shown in table 900, the mannose functional polycarbonate (e.g., mannose_16) and the glucose functional polycarbonate (glucose_17) respectively demonstrate low $ED_{50}$ and $ED_{95}$ values (e.g., less than 7.0 mg/kg for $ED_{50}$ and less than 21 for $ED_{95}$ mg/kg). In this regard, both mannose_16 and glucose_17 are highly effective against A. baumannii in vivo at relatively low effective doses. In addition, mannose_16 exhibits a lower $ED_{50}$ and $ED_{95}$ than imipenem and Dp20, demonstrating improved in vivo efficacy. Furthermore glucose_17 exhibits a lower $ED_{50}$ than Dp20 and a lower $ED_{95}$ than imipenem and Dp20.

In addition to the $ED_{50}$ and $ED_{95}$ evaluations described above, the efficacy of mannose_16 and glucose_17 was also tested for effectiveness over time using the immunosuppressed mice described above. In this regard, immunosuppressed mice were randomly divided into five groups, 25 in each group. The immunosuppressed mice were then injected with $1.5\times10^8$ CFUs of A. baumannii 4123 via the tail vein. Then each group of mice were injected intraperitoneally with either imipenem, dp20, mannose_16, glucose_17 or PBS, 1.0 hour and 6.0 hours after infection at doses of $ED_{50}$ (e.g., 6.1 mg/kg for imipenem, 8.3 mg/kg for dp20, 5.6 mg/kg for mannose_16 and 6.6 mg/kg for glucose_17). The PBS-treated group was used as the control. At 1.0 hour, 4.0 hours, 8.0 hours and 24 hours post-infection, five anesthetized mice in each group were sacrificed and blood samples were obtained from the periorbital plexus. The blood samples were subsequently serially diluted and plated on an MH agar plate. After being incubated at 37° C. overnight, the number of viable bacteria was counted. The results are presented in FIG. 10. Further, at 24 hours post infection, 5.0 mice in each group were sacrificed to acquire their organs including liver, spleen, kidney and lung. Obtained organs were homogenized in 2.0 mL of PBS. The homogenate samples were also serially diluted and plated on MH agar plates and incubated overnight at 37° C. The number of bacterial colonies in the respective samples was then counted. The results were showed as mean Log 10 (Lg) (CFU/mL)±standard deviation (SD), and are presented in FIG. 11.

Figure 10:
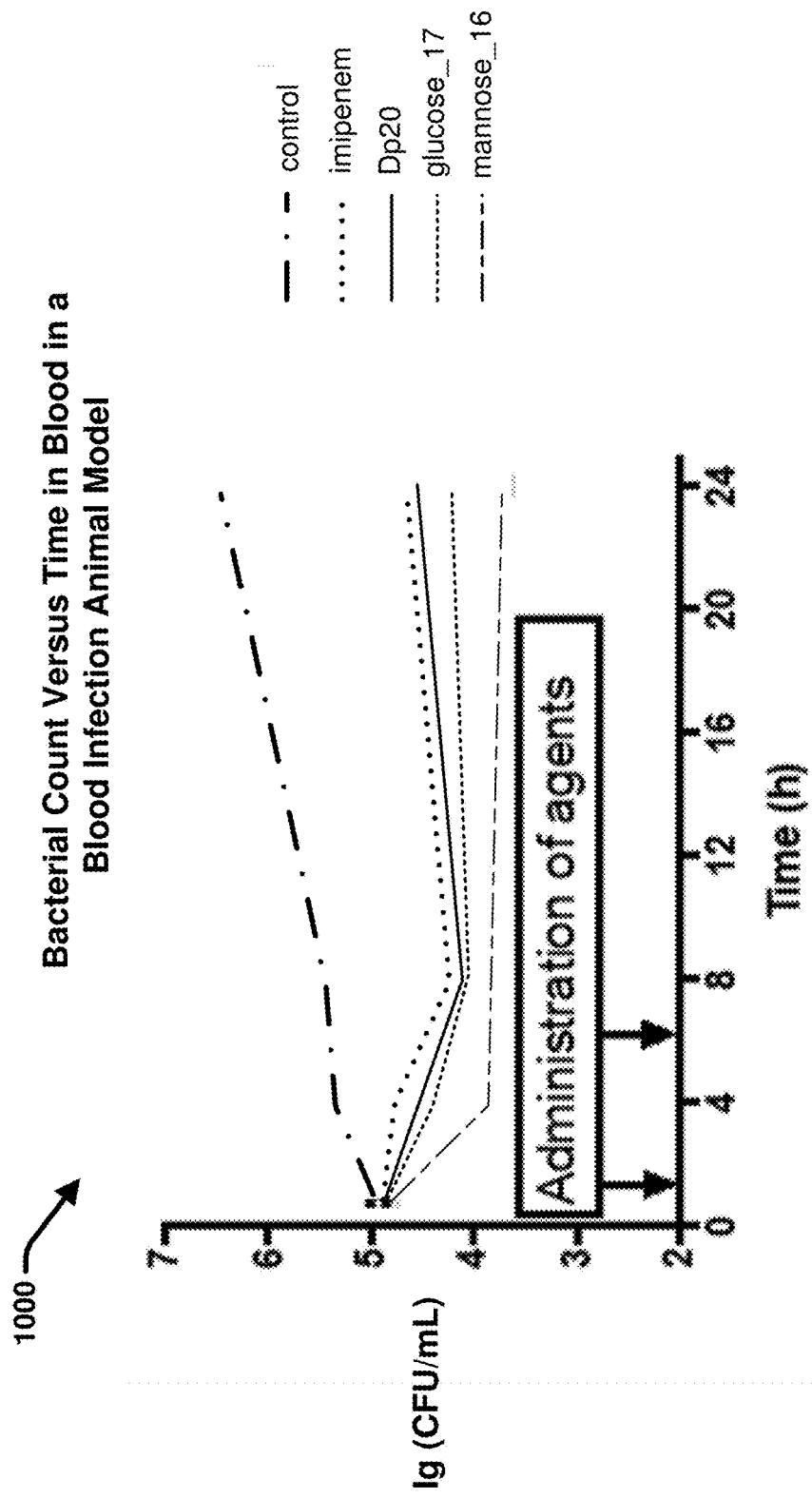
FIG. 10 presents an example, non-limiting graph demonstrating the efficacy of various antimicrobials, including the subject antimicrobial guanidinium macromolecules, against *A. baumannii* in a blood infected mouse model, accordance with one or more embodiments described herein.

FIG. 10 presents an example, non-limiting graph 1000 demonstrating the results of the above described mouse model testing the efficacy of various antimicrobials, including the subject guanidinium-based macromolecules, against A. baumannii over time. In this regard, graph 1000 charts the bacterial count observed in the infected mice as a function of time (e.g., tested at the 1.0, 4.0, 8.0, and 24-hour marks) following the administration two doses (one at 1.0 hour post infection and another at 6.0 hour post infection) of the therapeutics imipenem. Dp20, mannose_16 and glucose_17. As shown in graph 1000, the glucose and mannose-based polymers led to a rapid and significant decrease in bacterial count relative to the optimized antibiotic imipenem. Mannose_16 and glucose_17 also demonstrated a more rapid and overall higher decrease in bacterial count over time relative to Dp20.

Figure 11:
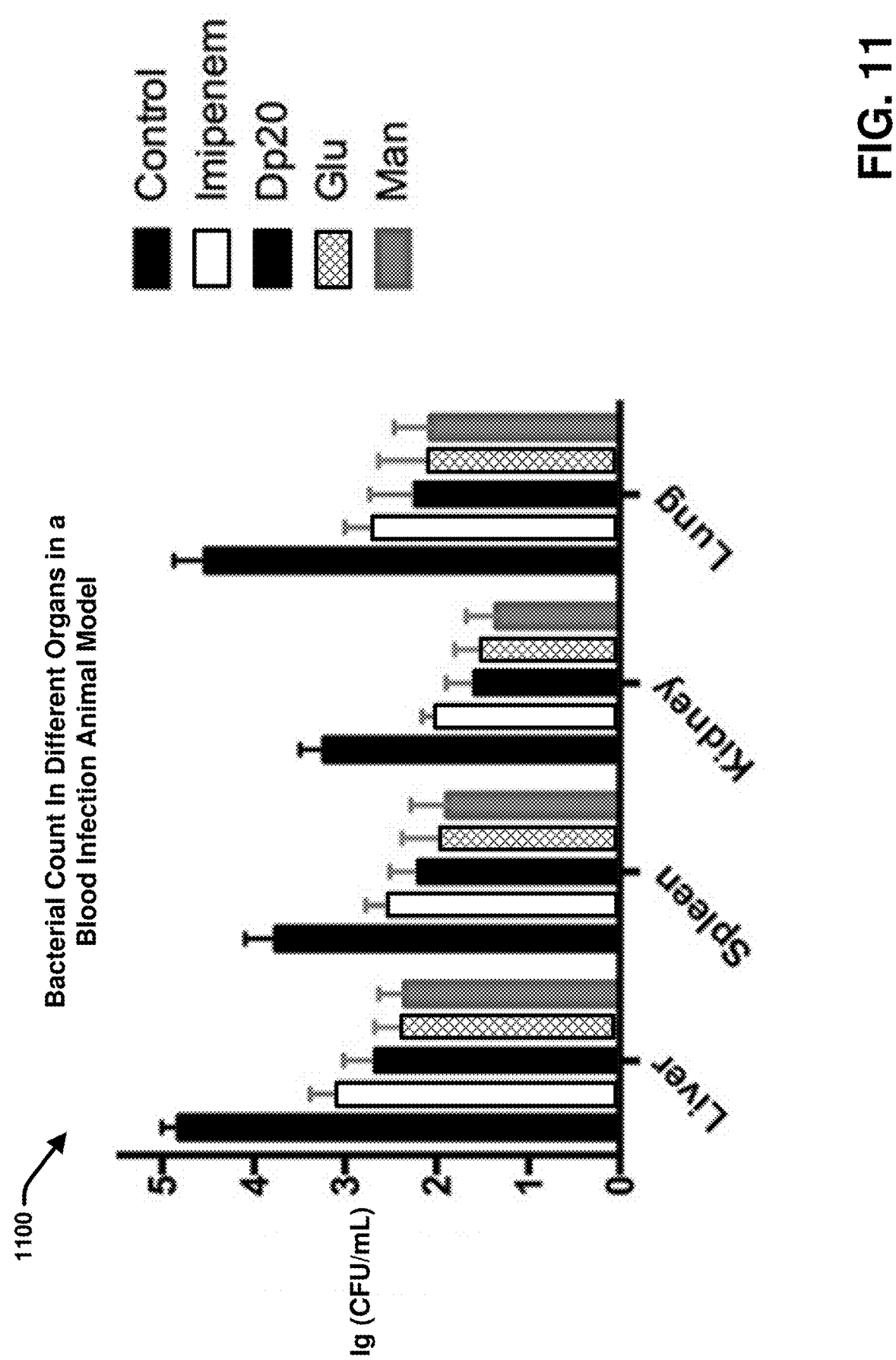
FIG. 11 illustrates another example, non-limiting graph that demonstrates the efficacy of various antimicrobials, including the subject antimicrobial guanidinium macromolecules, against *A. baumannii* in a blood infected mouse model, accordance with one or more embodiments described herein.

FIG. 11 presents an example, non-limiting graph 1000 demonstrating the results of the above described mouse model testing the efficacy of various antimicrobials, including the subject guanidinium-based macromolecules, against A. baumannii over time. In this regard, graph 1100 particularly compares the bacterial count remaining in various organs of A. baumannii infected mice after a period of 24 hours and two doses (one at 1.0 hour post infection and another at 6.0 hours post infection) of either imipenem. Dp20, mannose_16, or glucose_17. As shown in graph 1100, mannose_16 proved most effective and glucose_17 proved second most effective at killing the bacteria relative to the other tested antimicrobials, regardless of the organ of infection. In this regard, clearly the sugar-decorated therapeutics manifested significantly lower bacteria counts in the liver, kidney and spleen relative to imipenem.

The various structures (e.g., described regarding FIGS. 1-3, 4A and 4B), compositions (e.g., described regarding FIGS. 1-11), and/or methods (e.g., described regarding FIGS. 4A, 4B and FIGS. 5-11) described herein can regard chemical compounds that can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption.

Figure 12:
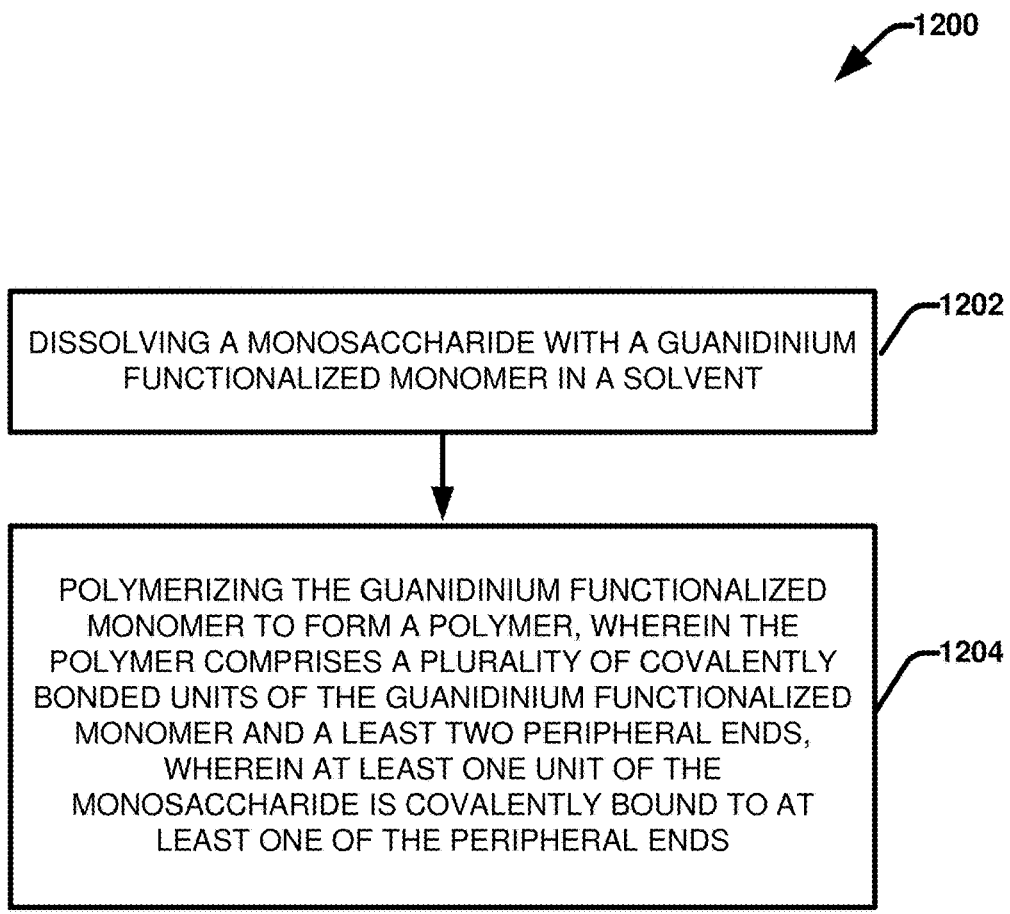
FIG. 12 illustrates a flow diagram of an example, non-limiting method that can facilitate generating one or more antimicrobial guanidinium macromolecules in accordance with one or more embodiments described herein.
Figure 13:
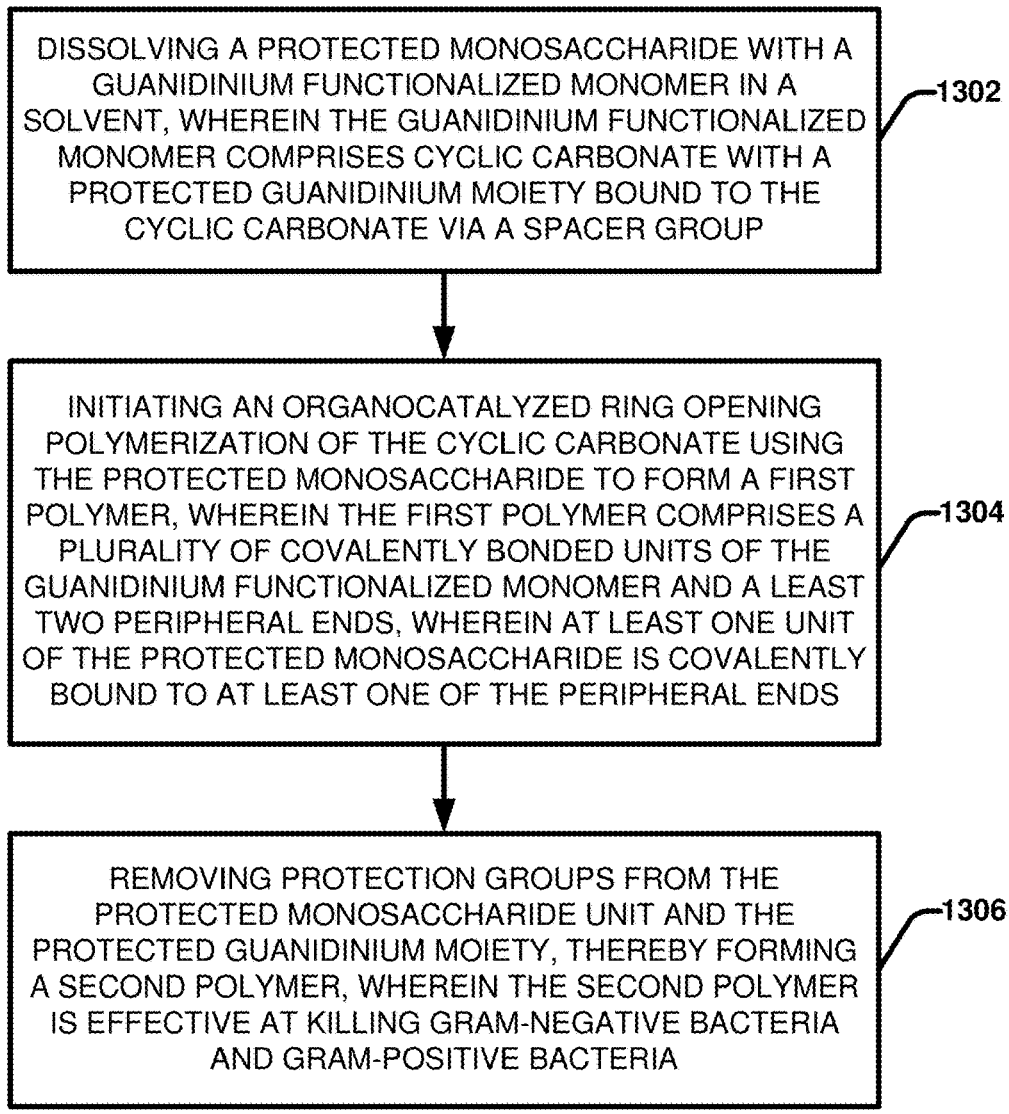
FIG. 13 illustrates a flow diagram of another example, non-limiting method that can facilitate generating one or more guanidinium macromolecules in accordance with one or more embodiments described herein.
Figure 14:
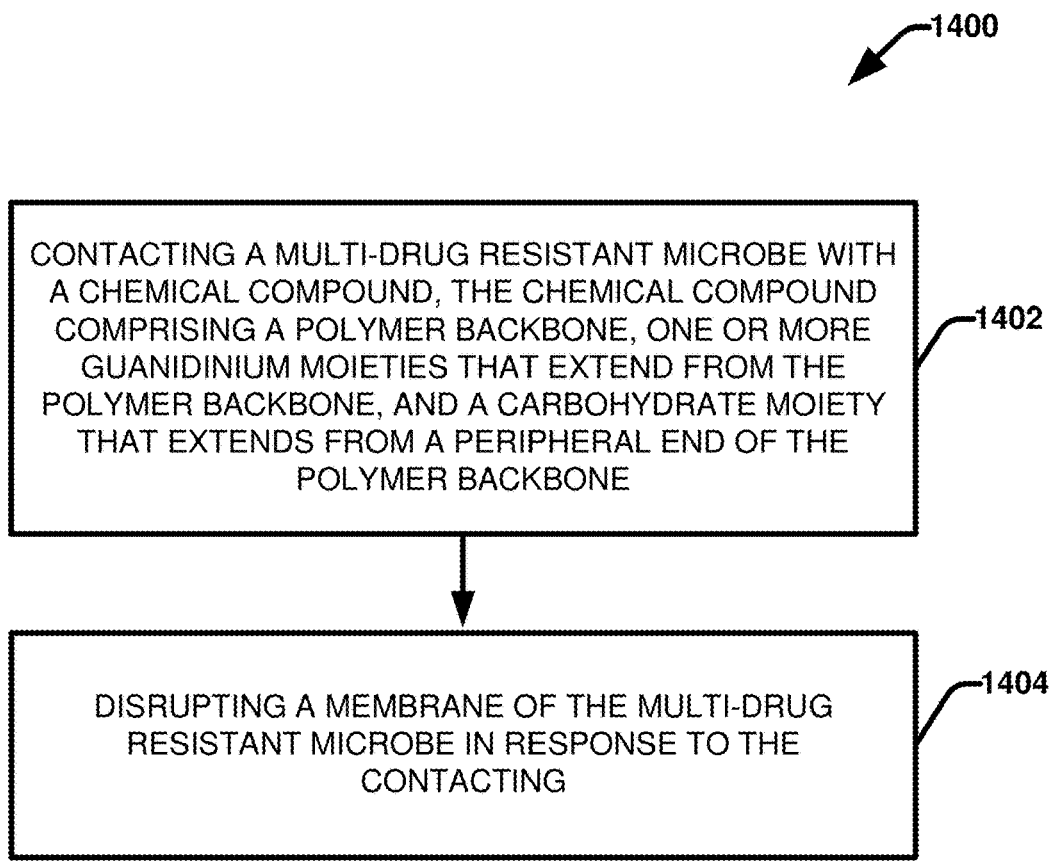
FIG. 14 illustrates a flow diagram of an example, non-limiting method that can facilitate killing of a pathogen with one or more guanidinium macromolecules in accordance with one or more embodiments described herein.

FIGS. 12-14 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts can occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts can be required to implement a methodology in accordance with the disclosed subject matter. Repetitive description of like elements employed in respective embodiments is omitted for sake of brevity.

FIG. 12 illustrates a flow diagram of an example, non-limiting method 1200 that can facilitate generating one or more antimicrobial guanidinium macromolecules in accordance with one or more embodiments described herein. At 1202, a monosaccharide can be dissolved with a guanidinium functionalized monomer in a solvent. As a result, at 1204 the guanidinium functionalized monomer can be polymerized to form a polymer, wherein the polymer comprises a plurality of covalently bonded units of the guanidinium functionalized monomer and a least two peripheral ends, wherein at least one unit of the monosaccharide is covalently bound to at least one of the peripheral ends.

FIG. 13 illustrates a flow diagram of another example, non-limiting method 1300 that can facilitate generating one or more guanidinium macromolecules in accordance with one or more embodiments described herein. At 1302, a protected monosaccharide can be dissolved with a guanidinium functionalized monomer in a solvent, wherein the guanidinium functionalized monomer comprises cyclic carbonate with a protected guanidinium moiety bound to the cyclic carbonate via a spacer group. At 1304, an organocatalyzed ring opening polymerization of the cyclic carbonate can be initiated using the protected monosaccharide to form a first polymer, wherein the first polymer comprises a plurality of covalently bonded units of the guanidinium functionalized monomer and a least two peripheral ends, wherein at least one unit of the protected monosaccharide is covalently bound to at least one of the peripheral ends. At 1306, protection groups from the protected monosaccharide and the protected guanidinium moiety can be removed, thereby forming a second polymer, wherein the second polymer is effective at killing Gram-negative bacteria and Gram-positive bacteria.

FIG. 14 illustrates a flow diagram of an example, non-limiting method 1400 that can facilitate killing of a pathogen with one or more guanidinium macromolecules in accordance with one or more embodiments described herein. At 1402, a MDR (MDR) microbe with a chemical compound (e.g., an antimicrobial guanidinium-based macromolecule having Structure 100, Structure, I, Structure II, Structure III, Structure IV, mannose_16, glucose_17, galactose_18, fructose_16, and the like). In this regard, the chemical compound comprises a polymer backbone, one or more guanidinium moieties that extend from the polymer backbone, and a carbohydrate moiety that extends from a peripheral end of the polymer backbone. At 1404, the method further comprises, disrupting a membrane of the MDR microbe in response to the contacting. For example, in one or more implementations, the carbohydrate moiety can selectively attract the microbe, resulting in consumption of the macromolecule by the microbe. The macromolecule is then released through the membrane leading to cytosol precipitation and subsequent bacterial cell apoptosis occurs. Moreover, the carbohydrate targeting moieties that comprise sugars have been shown to target the bacteria cell wall/membrane in such a way that the sugar gets taken up and chemically incorporated into the bacterial cell wall/membrane. Accordingly, in addition to facilitating targeting selectivity and antimicrobial efficiency of the guanidinium based macromolecule, the sugar moiety can further contribute to local disorder and stress within the lipid bilayer of the bacterial cell, leading to the membrane damage and thus a higher rate of cell lysis/apoptosis.

In addition, the term "or" is intended to mean an inclusive "or" rather than an exclusive "or." That is, unless specified otherwise, or clear from context. "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An antimicrobial polymer comprising a structure characterized by Structure I:

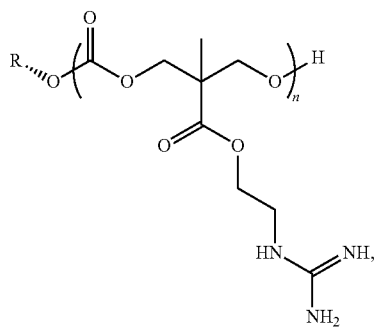

Structure I wherein R comprises a single unit of a monosaccharide moiety selected from the group consisting of glucose, fructose and galactose, wherein n comprises an integer greater than or equal to one and less than or equal to one thousand, and wherein X comprises a spacer group selected from a group consisting of: a propyl group, a butyl group, a pentyl group, a cyclohexyl group, a phenyl group, and a benzyl group.

2. The antimicrobial polymer of claim 1, wherein the antimicrobial polymer is more effective at killing Gram-negative bacteria and Gram-positive bacteria relative to a version of the antimicrobial polymer with the R group removed.

3. The antimicrobial polymer of claim 1, wherein the antimicrobial polymer is effective at killing multi-drug resistant bacteria selected from a group consisting of: *Acinetobacter baumannii, Klebsiella pneumonia, Escherichia coli, Staphylococcus aureus*, methicillin-resistant *Staphylococcus aureus*, and *Pseudomonas aeruginosa*.

4. The antimicrobial polymer of claim 1, wherein the antimicrobial polymer exhibits low toxicity in mammalian cells demonstrated by a red blood cell viability level greater than 95% at an effective dose.

5. The antimicrobial polymer of claim 1, wherein the antimicrobial polymer is attributed to no development of bacterial antimicrobial resistance over at least 20 passages.

6. The antimicrobial polymer of claim 2, wherein the antimicrobial polymer provides greater selectivity towards the Gram-positive bacteria and the Gram-negative bacteria relative to the version of the antimicrobial polymer without the R group.

7. The antimicrobial polymer of claim 2, wherein the antimicrobial polymer provides lower toxicity towards mammalian cells relative to the version of the antimicrobial polymer without the R group.

8. The antimicrobial polymer of claim 2, wherein the antimicrobial polymer is attributed with reduced antimicrobial resistance development relative to the version of the antimicrobial polymer without the R group.

* * * * *